(12) United States Patent
Somberg et al.

(10) Patent No.: US 7,700,310 B2
(45) Date of Patent: *Apr. 20, 2010

(54) METHOD FOR DETECTING TRANSFERASE ENZYMATIC ACTIVITY

(75) Inventors: Richard Somberg, Madison, WI (US); Said A. Goueli, Madison, WI (US)

(73) Assignee: Promega Corporation, Madison, WI (US)

(*) Notice: Subject to any disclaimer, the term of this patent is extended or adjusted under 35 U.S.C. 154(b) by 1134 days.

This patent is subject to a terminal disclaimer.

(21) Appl. No.: 10/655,878

(22) Filed: Sep. 5, 2003

(65) Prior Publication Data

US 2004/0101922 A1 May 27, 2004

Related U.S. Application Data

(60) Provisional application No. 60/408,662, filed on Sep. 6, 2002.

(51) Int. Cl.
*C12Q 1/48* (2006.01)
(52) U.S. Cl. ...................................................... 435/15
(58) Field of Classification Search ........................ None
See application file for complete search history.

(56) References Cited

U.S. PATENT DOCUMENTS

| | | | | |
|---|---|---|---|---|
| 4,390,274 | A | 6/1983 | Berthold et al. | 356/36 |
| 5,648,232 | A | 7/1997 | Squirrell | |
| 5,741,635 | A | 4/1998 | Boss et al. | 435/4 |
| 6,319,898 | B1 | 11/2001 | Davies et al. | |
| 6,599,711 | B2 | 7/2003 | Crouch et al. | 435/15 |
| 6,911,319 | B2 | 6/2005 | Crouch et al. | |
| 7,083,911 | B2 | 8/2006 | Wood et al. | |
| 2004/0253658 | A1* | 12/2004 | Crouch et al. | 435/15 |

FOREIGN PATENT DOCUMENTS

| | | |
|---|---|---|
| DE | 689 05 373 T2 | 3/1993 |
| DE | 37 86 279 T2 | 6/1993 |
| DE | 689 12 950 T2 | 2/1994 |
| DE | 694 09 830 T2 | 4/1998 |
| DE | 694 12 790 T2 | 8/1998 |
| EP | 0 022 432 | 1/1981 |
| EP | 1 041 151 A1 | 10/2000 |
| WO | WO 97/48803 | 12/1997 |
| WO | WO 98/37096 | 8/1998 |
| WO | WO 98/39444 | 9/1998 |
| WO | WO 99/09199 | 2/1999 |
| WO | WO 99/26657 | 6/1999 |
| WO | WO 00/50631 | 8/2000 |
| WO | WO 02/48390 | 6/2002 |
| WO | WO 02/48390 A2 | 6/2002 |
| WO | WO 02/066671 A2 | 8/2002 |

OTHER PUBLICATIONS

Simpson WJ and Hammond JRM (1991) The effect of detergents on firefly luciferase reactions. J Bioluminescence and Chemiluminescence vol. 6: pp. 97-106.*
Lev S, Givol D, and Yarden Y (1991) A specific combination of substrates is involved in signal transduction by the kit-encoded receptor. EMBO J vol. 10: pp. 647-654.*
Briggs SD, Lener EC, Smithgall TE (2000) Affinity of Src family kinase SH3 domains for HIV Nef in vitro does not predict kinase activation by Nef in vivo. Biochemistry vol. 39: pp. 489-495.*
Kapoor, et al., "Pyruvate Kinase of *Neurospora crasse*. Effect of Various Ligands on the Rate of Inactivation by Protein Denaturants", *Can. J. Microbiol.*, 1972, vol. 18, No. 8, pp. 1221-1232.
Lehel, et al., *Analytical Biochemistry*, 1997, vol. 244, pp. 340-346.
Lundin, et al., *Analytical Biochemistry*, 1976, vol. 75, pp. 611-620.
McDonald, et al., *Analytical Biochemistry*, 1999, vol. 268, pp. 318-329.
Näslund, et al., *Clinical Chemistry*, 1998, vol. 44, No. 9, pp. 1964-1973.
Promega Corporation Technical Bulletin No. 318, "Kinase-Glo™ Luminscent Kinase Assay", Dec. 2002.
Robbins, et al., *The Journal of Biological Chemistry*, Mar. 5, 1993, vol. 268, No. 7, pp. 5097-5106.
Brolin, et al., *Journal of Bioluminescence and Chemiluminescence*, 1989, vol. 4, pp. 446-453.
Brovko, et al., Biokhimiya, May 1978, vol. 43, No. 5, pp. 798-805.
Eriksson, et al., *Analytical Biochemistry*, 2001, vol. 293, pp. 67-70.
Eu, et al., *Analytical Biochemistry*, 1999, vol. 271, pp. 168-176.
Gonzalez, et al., *Analytical Biochemistry*, 1993, vol. 215, pp. 184-189.
Handa, et al., *Analytical Biochemistry*, 1980, vol. 102, pp. 332-339.
Hanocq-Quertier, et al., *Journal of Bioluminscence and Chemiluminiscence*, 1988, vol. 2, pp. 17-24.
Karamohamed, et al., *Analytical Biochemistry*, 1999, vol. 271, pp. 81-85.
Khokhlatchev, et al., *The Journal of Biological Chemistry*, Apr. 25, 1997, vol. 272, No. 17, pp. 11057-11062.
Ahn, et al., *J. Neurochem.*, Jul. 1992, vol. 59, No. 1, pp. 147-156 (abstract only).
Babcook, et al., *Anal. Biochem.*, Aug. 1, 1991, vol. 196, No. 2, pp. 245-251 (abstract only).

(Continued)

*Primary Examiner*—Ralph Gitomer
(74) *Attorney, Agent, or Firm*—McDonnell Boehnen Hulbert & Berghoff LLP

(57) ABSTRACT

Methods and kits for detecting transferase activity in a sample by measuring ATP using a composition comprising an ATP-dependent bioluminescence-generating enzyme, a luminogenic molecule and one or more transferase quenching agents.

20 Claims, 5 Drawing Sheets

OTHER PUBLICATIONS

Bachy, et al., *Journal of Immunological Methods*, 1999, vol. 230, pp. 37-46.
Branchini, et al., *Biochemistry*, 1999, vol. 38, pp. 13223-13230.
Branchini, et al., *Biochemistry*, 2000, vol. 39, pp. 5433-5440.
Builder, et al., *The Journal of Biological Chemistry*, Apr. 25, 1980, vol. 255. No. 8, pp. 3514-3519.
Cho, et al., *The Oncologist*, 1996, vol. 1, pp. 120-124.
Cohen, et al., *Analytical Biochemistry*, 1999, vol. 273, pp. 89-97.
D'Atri, et al., *Int. J. Tiss. Reac.*, 1986, vol. VIII (5), pp. 383-390.
Decker, et al., *Journal of Immunological Methods*, 1988, vol. 25, pp. 61-69.
Devine, et al., *Biochemica et Biophysica Acta*, 1993, vol. 1173, pp. 121-132.
Feutren, et al., *Journal of Immunological Methods*, 1984, vol. 75, pp. 85-94.
Glass, et al., *J. Biol. Chem.*, Oct. 10, 1979, vol. 254, No. 19, pp. 9728-9738 (abstract only).
Golding, et al., *The Journal of Experimental Biology*, 1995, vol. 198, pp. 1775-1782.
Handa, et al., *Plant Physiol.*, 1977, vol. 59, pp. 490-496.
Karamohamed, et al., *Biotechniques*, Apr. 1999, vol. 26, pp. 728-734.
Karp, et al., *Biomolecular Engineering*, 1999, vol. 16, pp. 101-104.
Kuo, et al., *Advances in Cyclic Nucleotide Research*, vol. 2, 1972, pp. 41-50.
Nociari, et al., *Journal of Immunological Methods*, 1998, vol. 213, pp. 157-167.
Olsson, et al., *Journal of Applied Biochemistry*, 1983, vol. 5, pp. 437-445.
Pastorino, et al., *The Journal of Biological Chemistry*, Oct. 29, 1999, vol. 274, No. 44, pp. 31734-31739.
Sala-Newby, et al., *FEBS*, Jul. 1992, vol. 307, No. 2, pp. 241-244.
Seethala, et al., *Analytical Biochemistry*, Nov. 15, 1997, vol. 253 (2), pp. 210-218 (abstract only).
Seethala, et al., *Analytical Biochemistry*, 1998, vol. 255, pp. 257-262.
Seger, et al., *The Journal of Biological Chemistry*, Jul. 15, 1992, vol. 267, No. 20, pp. 14373-14381.
Tatsumi, et al., *Analytical Biochemistry*, 1996, vol. 243, pp. 176-180.
Teague, et al., *The Journal of Experimental Biology*, 1996, vol. 199, pp. 509-512.
Anders Thore, *Science Tools*, 1979, vol. 26, No. 2, pp. 30-34.
White, et al., *Biochem J.*, 1996, vol. 319, pp. 343-350.
Kasatori, et al., *Jpn J Clin Pathol*, 1994, vol. 42, pp. 1050-1054.
Alexandre et al., *Journal of Virological Methods*, vol. 66, pp. 113-123, 1997.
Bessho et al., *J. Nutr. Sci. Vitaminol.*, vol. 34, pp. 607-614, 1988.
Handa et al., Analytical Biochemistry, vol. 102, pp. 332-339, 1980.
Idahl et al., Analytical Biochemistry, vol. 155, pp. 177-181, 1986.
Ugarova et al., Analytical Biochemistry, vol. 158, pp. 1-5, 1986.
Kapoor et al., Pyruvate Kinase of *Neurospora crassa*: effect of various ligands on the rate of inactivation by protein denaturants, Canadian Journal of Microbiology, 1972, pp. 1221-1232, vol. 18, NRC Research Press—National Research Council of Canada, Ottawa, Canada.

\* cited by examiner

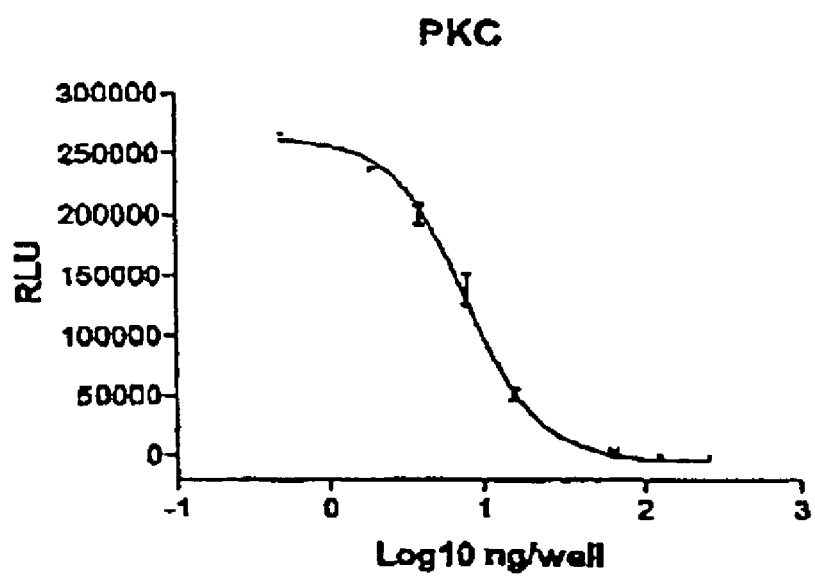
Figure 1. Results of PKC titration in a 96 well plate.
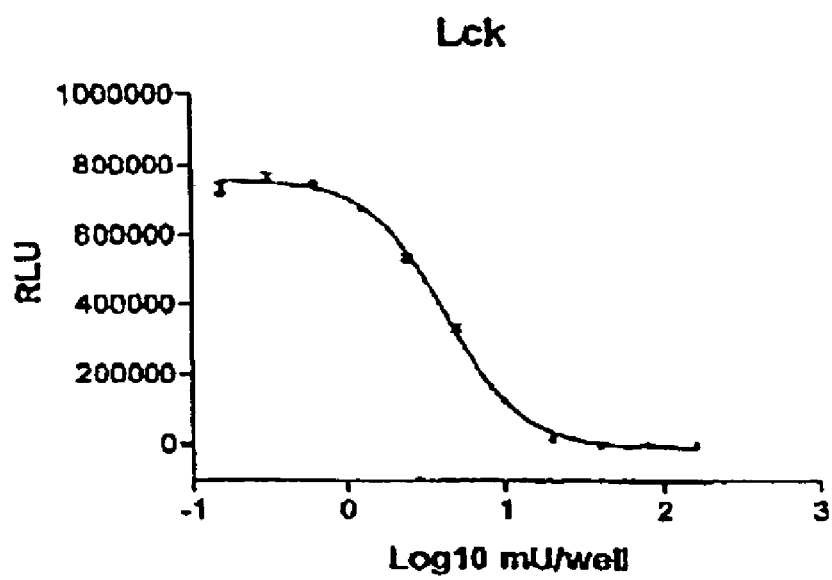
Figure 2. Results of Lck titration in a 96 well plate

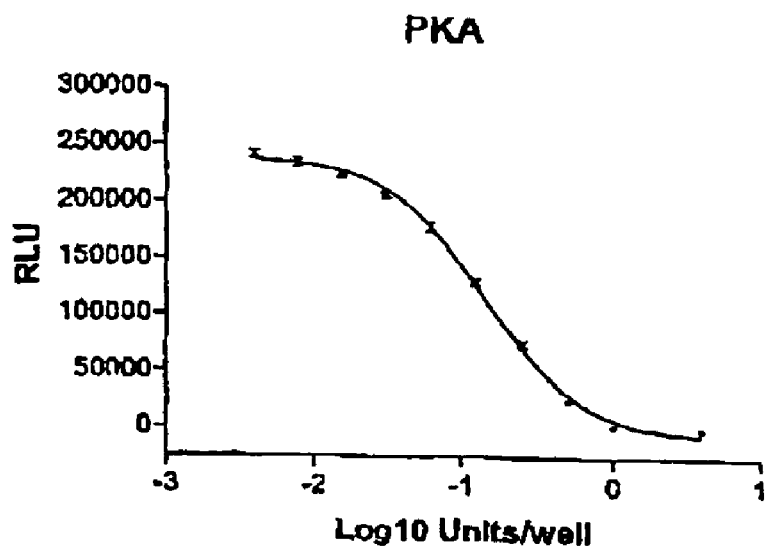
Figure 3. Results of PKA titration in a 96 well plate
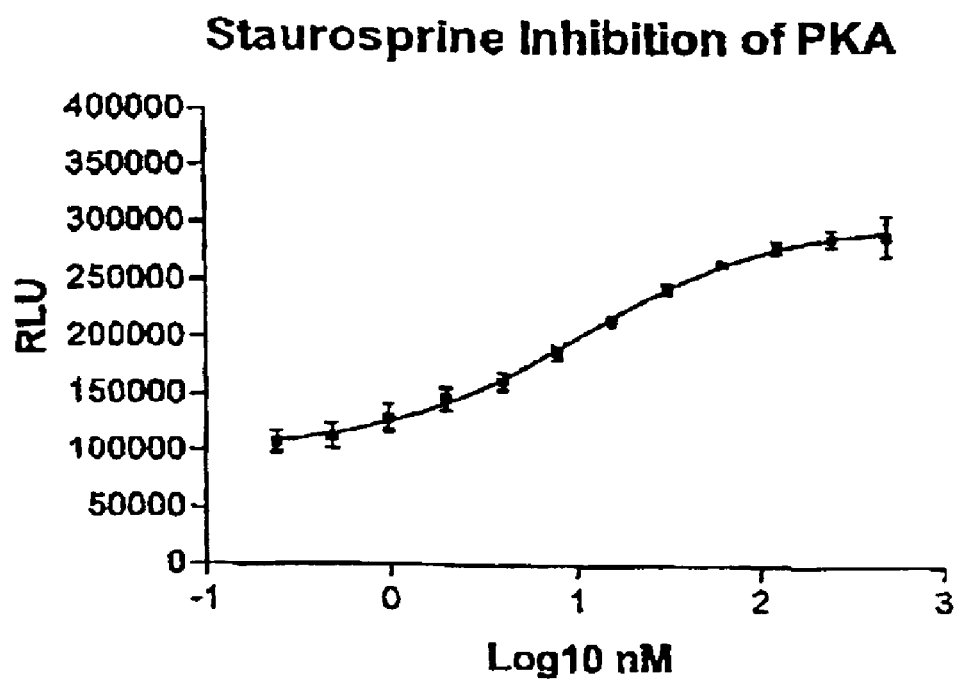
Figure 4 Staurosporine induced inhibition of PKA Z' analysis of PKA Assay Screening compounds from Plate 6 of the LOPAC library for inhibitors of PKA.

Signal stability of PKA Assay

SEQUENCE LISTING

<160> NUMBER OF SEQ ID NOS: 8

<210> SEQ ID NO 1
<211> LENGTH: 544
<212> TYPE: PRT
<213> ORGANISM: Photuris pennsylvanica

<400> SEQUENCE: 1

```
Met Ala Asp Lys Asn Ile Leu Tyr Gly Pro Glu Pro Phe Tyr Pro Leu
 1               5                  10                  15

Ala Asp Gly Thr Ala Gly Glu Gln Met Phe Asp Ala Leu Ser Arg Tyr
            20                  25                  30

Ala Asp Ile Ser Gly Cys Ile Ala Leu Thr Asn Ala His Thr Lys Glu
        35                  40                  45

Asn Val Leu Tyr Glu Glu Phe Leu Lys Leu Ser Cys Arg Leu Ala Glu
    50                  55                  60

Ser Phe Lys Lys Tyr Gly Leu Lys Gln Asn Asp Thr Ile Ala Val Cys
65                  70                  75                  80

Ser Glu Asn Gly Leu Gln Phe Phe Leu Pro Val Ile Ala Ser Leu Tyr
                85                  90                  95

Leu Gly Ile Ile Ala Ala Pro Val Ser Asp Lys Tyr Ile Glu Arg Glu
            100                 105                 110

Leu Ile His Ser Leu Gly Ile Val Lys Pro Arg Ile Ile Phe Cys Ser
        115                 120                 125

Lys Asn Thr Phe Gln Lys Val Leu Asn Val Lys Ser Lys Leu Lys Ser
    130                 135                 140

Val Glu Thr Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
            180                 185                 190

Leu Val Met Phe Ser Ser Gly Thr Thr Gly Val Pro Lys Gly Val Met
        195                 200                 205

Leu Thr His Lys Asn Ile Val Ala Arg Phe Ser Leu Ala Lys Asp Pro
    210                 215                 220

Thr Phe Gly Asn Ala Ile Asn Pro Thr Thr Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Val Glu Lys Tyr Asp
    290                 295                 300

Leu Ser His Leu Lys Glu Ile Ala Ser Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Lys Gly Asp Ala Arg Pro Gly Ser Thr Gly Lys Ile Val Pro Phe His
```

-continued

```
            355                 360                 365
Ala Val Lys Val Val Asp Pro Thr Thr Gly Lys Ile Leu Gly Pro Asn
    370                 375                 380

Glu Pro Gly Glu Leu Tyr Phe Lys Gly Ala Met Ile Met Lys Gly Tyr
385                 390                 395                 400

Tyr Asn Asn Glu Glu Ala Thr Lys Ala Ile Ile Asp Asn Asp Gly Trp
                405                 410                 415

Leu Arg Ser Gly Asp Ile Ala Tyr Tyr Asp Asn Asp Gly His Phe Tyr
                420                 425                 430

Ile Val Asp Arg Leu Lys Ser Leu Ile Lys Tyr Lys Gly Tyr Gln Val
                435                 440                 445

Ala Pro Ala Glu Ile Glu Gly Ile Leu Leu Gln His Pro Tyr Ile Val
    450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asp Phe Val Ser Ser Gln Val Ser Thr Ala Lys Trp Leu Arg
                500                 505                 510

Gly Gly Val Lys Phe Leu Asp Glu Ile Pro Lys Gly Ser Thr Gly Lys
                515                 520                 525

Ile Asp Arg Lys Val Leu Arg Gln Met Phe Glu Lys His Thr Asn Gly
                530                 535                 540
```

<210> SEQ ID NO 2
<211> LENGTH: 544
<212> TYPE: PRT
<213> ORGANISM: Photuris pennsylvanica

<400> SEQUENCE: 2

```
Met Ala Asp Lys Asn Ile Leu Tyr Gly Pro Glu Pro Phe Tyr Pro Leu
1               5                   10                  15

Glu Asp Gly Thr Ala Gly Glu Gln Met Phe Asp Ala Leu Ser Arg Tyr
                20                  25                  30

Ala Asp Ile Pro Gly Cys Ile Ala Leu Thr Asn Ala His Thr Lys Glu
            35                  40                  45

Asn Val Leu Tyr Glu Glu Phe Leu Lys Leu Ser Cys Arg Leu Ala Glu
        50                  55                  60

Ser Phe Lys Lys Tyr Gly Leu Lys Gln Asn Asp Thr Ile Ala Val Cys
65                  70                  75                  80

Ser Glu Asn Gly Leu Gln Phe Phe Leu Pro Val Ile Ala Ser Leu Tyr
                85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Val Phe Cys Ser
        115                 120                 125

Lys Asn Thr Phe Gln Lys Val Leu Asn Val Lys Ser Lys Leu Lys Ser
    130                 135                 140

Ile Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
            180                 185                 190
```

```
Leu Ile Met Phe Ser Ser Gly Thr Thr Gly Leu Pro Lys Gly Val Met
        195                 200                 205

Leu Thr His Lys Asn Ile Val Ala Arg Phe Ser Leu Ala Lys Asp Pro
    210                 215                 220

Thr Phe Gly Asn Ala Ile Asn Pro Thr Thr Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285

Thr Leu Met Ala Phe Leu Ala Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Lys Gly Asp Ala Lys Pro Gly Ser Thr Gly Lys Ile Val Pro Phe His
        355                 360                 365

Ala Val Lys Val Val Asp Pro Thr Thr Gly Lys Ile Leu Gly Pro Asn
    370                 375                 380

Glu Pro Gly Glu Leu Tyr Phe Lys Gly Pro Met Ile Met Lys Gly Tyr
385                 390                 395                 400

Tyr Asn Asn Glu Glu Ala Thr Lys Ala Ile Ile Asp Asn Asp Gly Trp
                405                 410                 415

Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
        435                 440                 445

Ala Pro Ala Glu Ile Glu Gly Ile Leu Leu Gln His Pro Tyr Ile Val
    450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asp Tyr Val Ala Ser Gln Val Ser Thr Ala Lys Trp Leu Arg
            500                 505                 510

Gly Gly Val Lys Phe Leu Asp Glu Ile Pro Lys Gly Ser Thr Gly Lys
        515                 520                 525

Ile Asp Arg Lys Val Leu Arg Gln Met Phe Glu Lys His Thr Asn Gly
    530                 535                 540

<210> SEQ ID NO 3
<211> LENGTH: 544
<212> TYPE: PRT
<213> ORGANISM: Photuris pennsylvanica

<400> SEQUENCE: 3

Met Ala Asp Lys Asn Ile Leu Tyr Gly Pro Glu Pro Phe Tyr Pro Leu
1               5                   10                  15

Glu Asp Gly Thr Ala Gly Glu Gln Met Phe Asp Ala Leu Ser Arg Tyr
            20                  25                  30
```

-continued

```
Ala Asp Ile Pro Gly Cys Ile Ala Leu Thr Asn Ala His Thr Lys Glu
         35                  40                  45

Asn Val Leu Tyr Glu Glu Phe Leu Lys Leu Ser Cys Arg Leu Ala Glu
 50                  55                  60

Ser Phe Lys Lys Tyr Gly Leu Lys Gln Asn Asp Thr Ile Ala Val Cys
 65                  70                  75                  80

Ser Glu Asn Ser Leu Gln Phe Phe Leu Pro Val Ile Ala Ser Leu Tyr
                 85                  90                  95

Leu Gly Ile Ile Val Ala Pro Val Asn Asp Lys Tyr Ile Glu Arg Glu
                100                 105                 110

Leu Ile His Ser Leu Gly Ile Val Lys Pro Arg Ile Val Phe Cys Ser
                115                 120                 125

Lys Asn Thr Phe Gln Lys Val Leu Asn Val Lys Ser Lys Leu Lys Ser
130                 135                 140

Ile Glu Thr Ile Ile Ile Leu Asp Leu Asn Asp Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
                180                 185                 190

Leu Ile Met Phe Ser Ser Gly Thr Thr Gly Leu Pro Lys Gly Val Met
                195                 200                 205

Leu Thr His Lys Asn Ile Val Ala Arg Phe Ser Ile Ala Lys Asp Pro
                210                 215                 220

Thr Phe Gly Asn Ala Ile Asn Pro Thr Ser Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
                260                 265                 270

Leu Gln Ser Leu Gln Asp Tyr Lys Val Glu Ser Thr Leu Leu Val Pro
                275                 280                 285

Thr Leu Met Ala Phe Leu Ala Lys Ser Ala Leu Val Glu Lys Tyr Asp
                290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
                340                 345                 350

Lys Gly Asp Ala Lys Pro Gly Ser Thr Gly Lys Ile Val Pro Phe His
                355                 360                 365

Ala Val Lys Val Val Asp Pro Thr Thr Gly Lys Ile Leu Gly Pro Asn
                370                 375                 380

Glu Pro Gly Glu Leu Tyr Phe Lys Gly Pro Met Ile Met Lys Gly Tyr
385                 390                 395                 400

Tyr Asn Asn Glu Glu Ala Thr Lys Ala Ile Ile Asp Asn Asp Gly Trp
                405                 410                 415

Leu Arg Ser Gly Asp Ile Ala Tyr Tyr Asp Asn Asp Gly His Phe Tyr
                420                 425                 430

Ile Val Asp Arg Leu Lys Ser Leu Ile Lys Tyr Lys Gly Tyr Gln Val
                435                 440                 445
```

```
Ala Pro Ala Glu Ile Glu Gly Ile Leu Leu Gln His Pro Tyr Ile Val
    450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asp Tyr Val Ala Ser Gln Val Ser Thr Ala Lys Trp Leu Arg
                500                 505                 510

Gly Gly Val Ile Phe Leu Asp Glu Ile Pro Lys Gly Ser Thr Gly Lys
                515                 520                 525

Ile Asp Arg Lys Val Leu Arg Gln Met Leu Glu Lys His Thr Asn Gly
530                 535                 540

<210> SEQ ID NO 4
<211> LENGTH: 544
<212> TYPE: PRT
<213> ORGANISM: Photuris pennsylvanica

<400> SEQUENCE: 4

Met Ala Asp Lys Asn Ile Leu Tyr Gly Pro Glu Pro Phe Tyr Pro Leu
1               5                   10                  15

Glu Asp Gly Thr Ala Gly Glu Gln Met Phe Asp Ala Leu Ser Arg Tyr
                20                  25                  30

Ala Ala Ile Pro Gly Cys Ile Ala Leu Thr Asn Ala His Thr Lys Glu
            35                  40                  45

Asn Val Leu Tyr Glu Glu Phe Leu Lys Leu Ser Cys Arg Leu Ala Glu
 50                 55                  60

Ser Phe Lys Lys Tyr Gly Leu Lys Gln Asn Asp Thr Ile Ala Val Cys
65                  70                  75                  80

Ser Glu Asn Ser Leu Gln Phe Phe Leu Pro Val Ile Ala Ser Leu Tyr
                85                  90                  95

Leu Gly Ile Ile Val Ala Pro Val Asn Asp Lys Tyr Ile Glu Arg Glu
            100                 105                 110

Leu Ile His Ser Leu Gly Ile Val Lys Pro Arg Ile Val Phe Cys Ser
        115                 120                 125

Lys Asn Thr Phe Gln Lys Val Leu Asn Val Lys Ser Lys Leu Lys Ser
130                 135                 140

Ile Glu Thr Ile Ile Ile Leu Asp Leu Asn Glu Asp Leu Gly Gly Tyr
145                 150                 155                 160

Gln Cys Leu Asn Asn Phe Ile Ser Gln Asn Ser Asp Ser Asn Leu Asp
                165                 170                 175

Val Lys Lys Phe Lys Pro Tyr Ser Phe Asn Arg Asp Asp Gln Val Ala
            180                 185                 190

Ser Ile Met Phe Ser Ser Gly Thr Thr Gly Leu Pro Lys Gly Val Met
        195                 200                 205

Leu Thr His Lys Asn Ile Val Ala Arg Phe Ser Ile Ala Lys Asp Pro
210                 215                 220

Thr Phe Gly Asn Ala Ile Asn Pro Thr Ser Ala Ile Leu Thr Val Ile
225                 230                 235                 240

Pro Phe His His Gly Phe Gly Met Met Thr Thr Leu Gly Tyr Phe Thr
                245                 250                 255

Cys Gly Phe Arg Val Val Leu Met His Thr Phe Glu Glu Lys Leu Phe
            260                 265                 270

Leu Gln Ser Leu Gln Asp Tyr Lys Val Glu Ser Thr Leu Leu Val Pro
        275                 280                 285
```

```
Thr Leu Met Ala Phe Leu Ala Lys Ser Ala Leu Val Glu Lys Tyr Asp
    290                 295                 300

Leu Ser His Leu Lys Glu Ile Ala Ser Gly Gly Ala Pro Leu Ser Lys
305                 310                 315                 320

Glu Ile Gly Glu Met Val Lys Lys Arg Phe Lys Leu Asn Phe Val Arg
                325                 330                 335

Gln Gly Tyr Gly Leu Thr Glu Thr Thr Ser Ala Val Leu Ile Thr Pro
            340                 345                 350

Lys Gly Asp Ala Lys Pro Gly Ser Thr Gly Lys Ile Val Pro Leu His
        355                 360                 365

Ala Val Lys Val Val Asp Pro Thr Thr Gly Lys Ile Leu Gly Pro Asn
    370                 375                 380

Glu Pro Gly Glu Leu Tyr Phe Lys Gly Pro Met Ile Met Lys Gly Tyr
385                 390                 395                 400

Tyr Asn Asn Glu Glu Ala Thr Lys Ala Ile Ile Asp Asn Asp Gly Trp
                405                 410                 415

Leu Arg Ser Gly Asp Ile Ala Tyr Tyr Asp Asn Asp Gly His Phe Tyr
            420                 425                 430

Ile Val Asp Arg Leu Lys Ser Leu Ile Lys Tyr Lys Gly Tyr Gln Val
        435                 440                 445

Ala Pro Ala Glu Ile Glu Gly Ile Leu Leu Gln His Pro Tyr Ile Val
    450                 455                 460

Asp Ala Gly Val Thr Gly Ile Pro Asp Glu Ala Ala Gly Glu Leu Pro
465                 470                 475                 480

Ala Ala Gly Val Val Gln Thr Gly Lys Tyr Leu Asn Glu Gln Ile
                485                 490                 495

Val Gln Asp Tyr Val Ala Ser Gln Val Ser Thr Ala Lys Trp Leu Arg
                500                 505                 510

Gly Gly Val Lys Phe Leu Asp Glu Ile Pro Lys Gly Ser Thr Gly Lys
            515                 520                 525

Ile Asp Arg Lys Val Leu Arg Gln Met Leu Glu Lys His Thr Asn Gly
        530                 535                 540

<210> SEQ ID NO 5
<211> LENGTH: 1639
<212> TYPE: DNA
<213> ORGANISM: Photuris pennsylvanica

<400> SEQUENCE: 5
ggatccaatg gcagataaga atattttata tgggcccgaa ccattttatc ccttggctga      60
tgggacggct ggagaacaga tgtttgacgc attatctcgt tatgcagata tttccggatg    120
catagcattg acaaatgctc atacaaaaga aaatgtttta tatgaagagt ttttaaaatt    180
gtcgtgtcgt ttagcggaaa gttttaaaaa gtatggatta aaacaaaacg acacaatagc    240
ggtgtgtagc gaaatggttt tgcaattttt ccttcctgta attgcatcat gtatcttgg     300 aataattgca gcacctgtta gtgataaata cattgaacgt gaattaatac acagtcttgg    360
tattgtaaaa ccacgcataa ttttttgctc caagaatact tttcaaaaag tactgaatgt    420
aaaatctaaa ttaaaatctg tagaaactat tattatatta gacttaaatg aagacttagg    480
aggttatcaa tgcctcaaca actttatttc tcaaaattcc gatagtaatc tggacgtaaa    540
aaaatttaaa ccatattctt ttaatcgaga cgatcaggtt cgttggtaa tgttttcttc     600 tggtacaact ggtgttccga agggagtcat gctaactcac aagaatattg ttgcacgatt    660
```

```
ttctcttgca aaagatccta cttttggtaa cgcaattaat cccacgacag caattttaac      720
ggtaatacct ttccaccatg gttttggtat gatgaccaca ttaggatact ttacttgtgg      780
attccgagtt gttctaatgc acacgtttga agaaaaacta tttctacaat cattacaaga      840
ttataaagtg gaaagtactt tacttgtacc aacattaatg gcatttcttg caaaaagtgc      900
attagttgaa aagtacgatt tatcgcactt aaaagaaatt gcatctggtg gcgcaccttt      960
atcaaaagaa attggggaga tggtgaaaaa acggtttaaa ttaaactttg tcaggcaagg     1020
gtatggatta acagaaacca cttcggctgt tttaattaca ccgaaaggtg acgccagacc     1080
gggatcaact ggtaaaatag taccatttca cgctgttaaa gttgtcgatc ctacaacagg     1140
aaaaattttg gggccaaatg aacctggaga attgtatttt aaaggcgcca tgataatgaa     1200
gggttattat aataatgaag aagctactaa agcaattatt gataatgacg gatggttgcg     1260
ctctggtgat attgcttatt atgacaatga tggccatttt tatattgtgg acaggctgaa     1320
gtcattaatt aaatataaag gttatcaggt tgcacctgct gaaattgagg gaatactctt     1380
acaacatccg tatattgttg atgccggcgt tactggtata ccggatgaag ccgcgggcga     1440
gcttccagct gcaggtgttg tagtacagac tggaaaatat ctaaacgaac aaatcgtaca     1500
agattttgtt tccagtcaag tttcaacagc caaatggcta cgtggtgggg tgaaattttt     1560
ggatgaaatt cccaaaggat caactggaaa aattgacaga aagtgttaa gacaaatgtt     1620 tgaaaaacac accaatggg                                                  1639

<210> SEQ ID NO 6
<211> LENGTH: 1639
<212> TYPE: DNA
<213> ORGANISM: Photuris pennsylvanica

<400> SEQUENCE: 6
ggatccaatg gcagataaga atattttata tgggcccgaa ccatttttatc ccttggaaga      60 tgggacggct ggagaacaga tgtttgacgc attatctcgt tatgcagata ttccgggctg     120
catagcattg acaaatgctc atacaaaaga aaatgtttta tatgaagagt ttctgaaact     180
gtcgtgtcgt ttagcggaaa gttttaaaaa gtatggatta aaacaaaacg acacaatagc     240
ggtgtgtagc gaaaatggtc tgcaattttt ccttcctgta attgcatcat tgtatcttgg     300
aataattgtg gcacctgtta acgataaata cattgaacgt gaattaatac acagtcttgg     360
tattgtaaaa ccacgcatag ttttttgctc caagaatact tttcaaaaag tactgaatgt     420
aaaatctaaa ttaaaatcta ttgaaactat tattatatta gacttaaatg aagacttagg     480
aggttatcaa tgcctcaaca actttatttc tcaaaattcc gatagtaatc tggacgtaaa     540
aaaatttaaa ccatattctt ttaatcgaga cgatcaggtt gcgttgatta tgttttcttc     600
tggtacaact ggtctgccga agggagtcat gctaactcac aagaatattg ttgcacgatt     660
ttctcttgca aaagatccta cttttggtaa cgcaattaat cccacgacag caattttaac     720
ggtaatacct ttccaccatg gttttggtat gatgaccaca ttaggatact ttacttgtgg     780
attccgagtt gttctaatgc acacgtttga agaaaaacta tttctacaat cattacaaga     840
ttataaagtg gaaagtactt tacttgtacc aacattaatg gcatttcttg caaaaagtgc     900
attagttgaa aagtacgatt tatcgcactt aaaagaaatt gcatctggtg gcgcaccttt     960
atcaaaagaa attggggaga tggtgaaaaa acggtttaaa ttaaactttg tcaggcaagg    1020
gtatggatta acagaaacca cttcggctgt tttaattaca ccgaaaggtg acgccaaacc    1080
gggatcaact ggtaaaatag taccatttca cgctgttaaa gttgtcgatc ctacaacagg    1140
```

```
aaaaattttg gggccaaatg aacctggaga attgtatttt aaaggcccga tgataatgaa    1200
gggttattat aataatgaag aagctactaa agcaattatt gataatgacg gatggttgcg    1260
ctctggtgat attgcttatt atgacaatga tggccatttt tatattgtgg acaggctgaa    1320
gtcactgatt aaatataaag gttatcaggt tgcacctgct gaaattgagg gaatactctt    1380
acaacatccg tatattgttg atgccggcgt tactggtata ccggatgaag ccgcgggcga    1440
gcttccagct gcaggtgttg tagtacagac tggaaaatat ctaaacgaac aaatcgtaca    1500
agattatgtt gccagtcaag tttcaacagc caaatggcta cgtggtgggg tgaaattttt    1560
ggatgaaatt cccaaaggat caactggaaa aattgacaga aaagtgttaa gacaaatgtt    1620
tgaaaaacac accaatggg                                                 1639

<210> SEQ ID NO 7
<211> LENGTH: 1639
<212> TYPE: DNA
<213> ORGANISM: Photuris pennsylvanica

<400> SEQUENCE: 7
agatccaatg gcagataaga atattttata tgggcccgaa ccattttatc ccttggaaga      60
tgggacggct ggagaacaga tgtttgacgc attatctcgt tatgcagata ttccgggctg     120
catagcattg acaaatgctc atacaaaaga aaatgtttta tatgaagagt ttctgaaact     180
gtcgtgtcgt ttagcggaaa gttttaaaaa gtatggatta aaacaaaacg acacaatagc     240
ggtgtgtagc gaaaatagtc tgcaattttt ccttcctgta attgcatcat tgtatcttgg     300 ataattgtg gcacctgtta acgataaata cattgaacgt gaattaatac acagtcttgg     360
tattgtaaaa ccacgcatag tttttgctc caagaatact tttcaaaaag tactgaatgt     420
aaaatctaaa ttaaaatcta ttgaaactat tattatatta gacttaaatg atgacttagg     480
aggttatcaa tgcctcaaca actttatttc tcaaaattcc gatagtaatc tggacgtaaa     540
aaaatttaaa ccatattctt ttaatcgaga cgatcaggtt gcgttgatta tgttttcttc     600
tggtacaact ggtctgccga agggagtcat gctaactcac aagaatattg ttgcacgatt     660
ttctattgca aaagatccta cttttggtaa cgcaattaat cccacgtcag caattttaac     720 ggtaataccct ttccaccatg gttttggtat gatgaccaca ttaggatact ttacttgtgg     780
attccgagtt gttctaatgc acacgtttga agaaaaacta tttctacaat cattacaaga     840
ttataaagtg gaaagtactt tacttgtacc aacattaatg gcatttcttg caaaaagtgc     900
attagttgaa aagtacgatt tatcgcactt aaaagaaatt gcatctggtg gcgcaccttt     960
atcaaaagaa attggggaga tggtgaaaaa acggtttaaa ttaaactttg tcaggcaagg    1020
gtatggatta acagaaacca cttcggctgt tttaattaca ccgaaaggtg acgccaaacc    1080
gggatcaact ggtaaaatag taccatttca cgctgttaaa gttgtcgatc ctacaacagg    1140
aaaaattttg gggccaaatg aacctggaga attgtatttt aaaggcccga tgataatgaa    1200
gggttattat aataatgaag aagctactaa agcaattatt gataatgacg gatggttgcg    1260
ctctggtgat attgcttatt atgacaatga tggccatttt tatattgtgg acaggctgaa    1320
gtcactgatt aaatataaag gttatcaggt tgcacctgct gaaattgagg gaatactctt    1380
acaacatccg tatattgttg atgccggcgt tactggtata ccggatgaag ccgcgggcga    1440
gcttccagct gcaggtgttg tagtacagac tggaaaatat ctaaacgaac aaatcgtaca    1500
agattatgtt gccagtcaag tttcaacagc caaatggcta cgtggtgggg tgatattttt    1560
```

-continued

```
ggatgaaatt cccaaaggat caactggaaa aattgacaga aaagtgttaa gacaaatgtt    1620
agaaaaacac accaatggg                                                 1639

<210> SEQ ID NO 8
<211> LENGTH: 1639
<212> TYPE: DNA
<213> ORGANISM: Photuris pennsylvanica

<400> SEQUENCE: 8
ggatccaatg gcagataaga atattttata tgggcccgaa ccattttatc ccttggaaga      60
tgggacggct ggagaacaga tgtttgacgc attatctcgt tatgcagcta ttccgggctg     120
catagcattg acaaatgctc atacaaaaga aaatgtttta tatgaagagt ttctgaaact     180
gtcgtgtcgt ttagcggaaa gttttaaaaa gtatggatta aaacaaaacg acacaatagc     240
ggtgtgtagc gaaaatagtc tgcaattttt ccttcctgta attgcatcat tgtatcttgg     300
aataattgtg gcacctgtta acgataaata cattgaacgt gaattaatac acagtcttgg     360
tattgtaaaa ccacgcatag ttttttgctc caagaatact tttcaaaaag tactgaatgt     420
aaaatctaaa ttaaaatcta ttgaaactat tattatatta gacttaaatg aagacttagg     480
aggttatcaa tgcctcaaca actttatttc tcaaaattcc gatagtaatc tggacgtaaa     540
aaaatttaaa ccctattctt ttaatcgaga cgatcaggtt gcgtcgatta tgttttcttc     600
tggtacaact ggtctgccga agggagtcat gctaactcac aagaatattg ttgcacgatt     660
ttctattgca aaagatccta ctttggtaa cgcaattaat cccacgtcag caattttaac     720
ggtaatacct ttccaccatg gttttggtat gatgaccaca ttaggatact ttacttgtgg     780
attccgagtt gttctaatgc acacgtttga agaaaaacta tttctacaat cattacaaga     840
ttataaagtg gaaagtactt tacttgtacc aacattaatg gcatttcttg caaaaagtgc     900
attagttgaa aagtacgatt tatcgcactt aaaagaaatt gcatctggtg gcgcaccttt     960
atcaaaagaa attggggaga tggtgaaaaa acggtttaaa ttaaactttg tcaggcaagg    1020
gtatggatta acagaaacca cttcggctgt tttaattaca ccgaaaggtg acgccaaacc    1080
gggatcaact ggtaaaatag taccattaca cgctgttaaa gttgtcgatc ctacaacagg    1140
aaaaattttg gggccaaatg aacctggaga attgtatttt aaaggcccga tgataatgaa    1200
gggttattat aataatgaag aagctactaa agcaattatt gataatgacg gatggttgcg    1260
ctctggtgat attgcttatt atgacaatga tggccatttt tatattgtgg acaggctgaa    1320
gtcactgatt aaatataaag gttatcaggt tgcacctgct gaaattgagg aatactctt    1380 acaacatccg tatattgttg atgccggcgt tactggtata ccggatgaag ccgcgggcga    1440
gcttccagct gcaggtgttg tagtacagac tggaaaatat ctaaacgaac aaatcgtaca    1500
agattatgtt gccagtcaag tttcaacagc caaatggcta cgtggtgggg tgaaattttt    1560
ggatgaaatt cccaaaggat caactggaaa aattgacaga aaagtgttaa gacaaatgtt    1620
agaaaaacac accaatggg                                                 1639
```

METHOD FOR DETECTING TRANSFERASE ENZYMATIC ACTIVITY

CROSS REFERENCE TO RELATED APPLICATIONS

This non-provisional application claims the benefit of priority to U.S. provisional application No. 60/408,662, filed Sep. 6, 2002 entitled METHOD FOR DETECTING TRANSFERASE ENZYMATIC ACTIVITY.

FIELD OF THE INVENTION

The present invention relates generally to the fields of enzymology and molecular biology. In particular, this invention relates to methods, compositions and kits for improving the detection and quantitation of transferase activity.

BACKGROUND OF THE INVENTION

Advances in the biological, biomedical and pharmaceutical sciences have accelerated the pace of research and diagnostics unparalleled to the past. With whole genome sequences becoming quickly and successively available, the assembly of large libraries of small molecules, and the ability to move pharmaceutical development, clinical diagnostic tests and basic research from a reductionist to a whole system approach demands assays that facilitate high throughput analyses. Molecules no longer need to be singly analyzed for their effects on a lone process; instead, the effects of many molecules on several biological systems can be studied simultaneously—if appropriate, fast, reliable, and accurate assays are available.

Due to their physiological relevance, variety and ubiquitousness, transferases, especially kinases, have become one of the most important and widely studied families of enzymes in biochemical and medical research. Studies have shown that protein and lipid kinases are key regulators of many cell functions, including signal transduction, transcriptional regulation, cell motility, cell division and cellular responses to drugs, toxins, and pathogens.

Protein kinases play crucial roles in the modulation of a wide variety of cellular events. These enzymes act by transferring phosphate residues to certain amino acids in intracellular polypeptides, to bring about the activation of these protein substrates, and set in motion a cascade of activation controlling events including the growth, differentiation and division of cells. Protein kinases have been extensively studied in the field of tumour biology. A lack of controlled activity of kinases in cells is believed to lead to the formation of tumours. The pharmaceutical industry is constantly in search of drugs that target these kinases, to help with the treatment of a wide variety of tumours. There are at least 1200 protein kinases that are involved in the regulation of cell functions. They occur as both transmembrane and cytosolic enzymes and they phosphorylate serine, threonine and tyrosine amino acid residues. Based on these substrate specificities the kinases are divided into two groups, the serine/threonine kinases and tyrosine kinases.

Serine/threonine kinases, includes cyclic AMP and cyclic GMP dependent protein kinases, calcium and phospholipid dependent protein kinase, calcium and calmodulin-dependent protein kinases, casein kinases, cell division cycle protein kinases and others. These kinases are usually cytoplasmic or associated with the particulate fractions of cells, possibly by anchoring proteins.

Tyrosine kinases phosphorylate tyrosine residues. These particular kinases are present in much smaller quantities but play an equally important role in cell regulation. These kinases include several soluble enzymes such as src family of protein kinases, and receptors for growth factors such as epidermal growth factor receptor, insulin receptor, and platelet derived growth factor receptor and others. Studies have indicated that many tyrosine kinases are transmembrane proteins with their receptor domains located on the outside of the cell and their kinase domains on the inside.

Lipid kinases also play important roles in the intracellular signal transduction, and have been grouped into four major classes. Exemplary lipid kinases include PI3 kinases, and phosphatidylinositol 4-kinases.

Current types of assays used to measure kinase activity and to detect potential kinase inhibitors are cumbersome and costly. These assays include Fluorescence Resonance Energy Transfer (FRET) assays, Fluorescent Plarization (FP) assays, and assays based on radioactivity such as Scintillation Proximity Assay (SPA).

FRET assays used to detect kinase activity utilize a protein substrate that has two linked fluorescent molecules. The two molecules are in close proximity, separated by a fixed distance. The energy of an excited electron in one molecule (the donor) is passed to an adjacent molecule (the acceptor) through resonance. The ability of a higher energy donor flourophore to transfer energy directly to a lower energy acceptor molecule causes sensitized fluorescence of the acceptor molecule and simultaneously quenches the donor flouorescence. In this case, the fluorescence of the donor is "quenched" by the proximity to the acceptor and the energy of the donor is transferred to the acceptor in a non-radiative manner. The efficiency of energy transfer is dependent on the distance between the donor and acceptor chromophores according to the Forster equation. In most cases, no FRET is observed at distances greater than 100 angstroms and thus the presence of FRET is a good indicator of close proximity.

In order for FRET to be useful, the fluorescence of the acceptor molecule must be significantly different from the fluorescence of the donor. A useful FRET based protein substrate may include a separation of the two fluorescent molecules via a peptide linker that maintains specificity for an endopeptidase that is capable of cleaving the peptide linker between the two fluorophores. If the peptide is phosphorylated, then the enzyme may not cleave the protein or may cleave it at a reduced rate, keeping the fluorescent molecules in close proximity such that quenching occurs. On the other hand, if the protein is not phosphorylated, then the endopeptidase cleaves the protein substrate, releasing the two fluorescent molecules such that the quenching is alleviated, and the two fluorescent molecules fluoresce independently. The FRET assay requires peptide substrates that must be carefully engineered to meet these requirements. That is, the peptide substrates must contain the enzyme recognition site required for the endopeptidase, the distance between the two fluorophores must be within the range to allow FRET to occur and the fluorescent molecules must be paired in such a way that donor fluorescence is significantly quenched, minimizing background fluorescence from the donor. Furthermore, the fluorescence of the starting material (the "quenched" substrate) must be siginificantly different from the product (the "released" non-quenched product). These requirements make a FRET based assay cumbersome and costly.

FP assays are based on binding of a high affinity binding reagent, such as an antibody, a chelating atom, or the like, to a fluorescent labeled molecule. For example, an antibody that binds to a phosphorylated fluorescent labeled peptide but not a non-phosphorylated fluorescent labeled peptide can be used for a kinase assay. When the fluorescent label is excited with plane polarized light, it emits light in the same polarized plane as long as the fluorescent label remains stationary throughout the excited state (duration of the excited state varies with fluorophore, and is 4 nanoseconds for fluoroscein). However, if the excited fluorescent label rotates or tumbles out of the plane of polarization during the excited state, then light is emitted in a different plane from that of the initial excitation state. If polarized light is used to excite the fluorophore, the emission light intensity can be monitored in both the plane parallel to the plane of polarization (the excitation plane) and in the plane perpendicular to the plane of polarization. The degree to which the emission intensity moves from the parallel to the perpendicular plane is related to the mobility of the fluorescent labeled molecule. If the fluorescent labeled molecules are large, such as when they are bound to the binding reagent, the fluorescent labeled molecules move little during the excited state interval, and emitted light remains highly polarized with respect to the excitation plane. If the fluorescent labeled molecules are small, such as when no binding reagent is bound to the fluorescent labeled molecules, the fluorescent labeled molecules rotate or tumble faster, and the resulting emitted light is depolarized relative to the excitation plane. Thus, an FP assay requires a high affinity binding reagent, e.g., an antibody, capable of binding with high specifity to the fluorescent labeled molecule. The time consuming and costly optimization of antibody binding with specific fluorescent labeled molecules such as peptides is required where antibodies are used. Additionally, the FP assay there is the potential for phosphorylated protein and other reaction components, e.g., lipids and detergents, to interfere with the polarization.

Kinase assays that use radioactive labels include SPA. In SPA, modified ligand-specific or ligand-capturing molecules are coupled to fluoromicrospheres, which are solid-phase support particles or beads impregnated with substances that emit energy when excited by radioactively labeled molecules. When added to a modified ligand such as radio-labeled phosphopeptide in a mixture with nonphosphorylated peptide, only the phosphopeptide is captured on a fluoromicrosphere, bringing any bound radiolabeled peptide close enough to allow the radiation energy emitted to activate the fluoromicrosphere and emit light energy. If the concentration of fluoromicrospheres is optimized, only the signal from the radio-labeled ligand bound to the target is detected, eliminating the need for any separation of bound and free ligand. The level of light energy emitted may be measured in a liquid scintillation counter and is indicative of the extent to which the ligand is bound to the target. However, a SPA requires radio-labeled ligands, which have disposal costs and possible health risks. In addition, a SPA requires the fluoromicrospheres to settle by gravity or be centrifuged, adding an additional step and time to the assay.

Other methods have been developed for detecting kinase activity that are based on luminescence detection, either by bioluminesce or chemiluminescences. Generally, these methods rely on specific substrates and antibodies (Lehel et al. (1977), the use of microchips and fluorescent label probes (Cohen et al. (1999), substrate concentration in a sample (Eu etal al (1999), the use of multiple steps and reagents (Crouch et al. U.S. Pat. No. 6,599,711) or are limited to specific kinases (Sala-Newby et al. (1992).

With phosphorylation events involved in so many cell functions and diseases, identifying transferase activity, especially kinase activity, is tremendously important. Thus, there is a need for enzyme assays that detect protein kinase activity, but that do not require large amounts of costly or highly specialized starting materials, that quickly generate results and are amendable to high through put screening. Additionally, there is a need for assays to rapidly identify activators and inhibitors of kinases. In addition, it is also desirable to provide kits for carrying out such assays. The method, system and kit associated with the present invention may be used for high throughput systems to allow the rapid detection and analysis of effectors, modulators, enhancers and inhibitors of one or more kinase. Moreover, the present invention allows the screening to be completed without the need for specially labeled substrates or antibodies.

SUMMARY OF THE INVENTION

The invention is drawn to methods, compositions and kits that are used for detection of transferase activity in a sample. The methods described herein are homogeneous, fast, sensitive, simple, and non-radioactive. The methods are convenient and can be used with any instrumentation platform. Reagents required can be designed with relative ease and may be synthesized readily. The methods provide assays with fast development time and low cost.

In one embodiment of the invention, a method for detecting kinase activity of a sample is provided. In a preferred embodiment, the sample is contacted with a kinase substrate, and at least one of a phosphate group donor (specifically ATP) and a phosphate group acceptor substrate or the enzyme itself (autophosphorylation) to form a reaction mixture. Kinase activity or the effect of a compound on kinase activity in a sample would result in a decrease or increase in the ATP levels in the sample.

Thereafter, a luminescent reporter with contacted with the reaction mixture. ATP interacts with a luminescent reporter compound and produces a luminescence signal that is directly proportional to the amount of ATP present. The luminescence output of the reporter compound is then detected, typically reported as Relative Light Units ("RLU"). An advantage of the present invention is that the kinase activity detection methods can be performed in a single well in a multi-well plate, making them suitable for use as high throughput screening methods. The method of the present invention may be optimized by altering the amounts of ATP and kinase substrate. In addition, increasing the reaction temperature may improve kinase activity.

The method of the present invention can be utilized to detect kinase activity over a wide range of ATP concentrations, generally from about 1 to about 100 µM of ATP. The method of present invention may be used to detect kinase activity at low concentration levels of ATP, generally below 5 µM of ATP, more preferably in the range of about 1 to about 3 µM of ATP.

In another embodiment of the invention, the method of detecting kinase activity comprises contacting a sample with a kinase substrate, at least one of a phosphate group donor (specifically ATP) and a phosphate group acceptor for a first predetermined time period to allow for sufficient opportunity for the kinase to interact with the kinase substrate. The resulting kinase reaction mixture is then contacted with a composition ("reagent composition") for a second predetermined time period. The reagent composition comprises a bioluminescence generating enzyme, a luminogenic molecule and a transferase quenching agent. Thereafter, the luminescence produced in the resulting reaction mixture is then detected. The luminescence is produced by the conversion of the luminogenic molecule into a luminescing compound by bioluminescence generating enzyme such as luciferase. This method can be used to measure a distinct end-point of a kinase reaction. The reagent composition allows, in a single step, for the simultaneous quenching or termination of transferase activity and generation of a luminescent signal that is directly proportional to the amount of ATP present.

The method is homogeneous and can be used for a wide variety of transferases such as protein kinases and lipid kinases and substrates such as amino acids, peptides, proteins (including fusion proteins and other kinases), sugars and lipids. The regent is robust and resulting luminescence is much less susceptible to interference by library compounds than other luciferase-based ATP detection reagents. In addition, the reagent composition facilitates measurement of transferase activity in a single sample over a long period of time as well as measurement of transferase activity in many samples in a high throughput format over a long period of time, thus eliminating the need for luminometers with reagent injectors and allowing for batch-mode processing of multiple samples.

In general, the methods comprise adding a composition ("reagent composition") comprising a bioluminesce generating enzyme such as a luciferase (such as exemplified by, but not limited to, SEQ ID NOs: 1-4), a luminogenic substrate such as luciferin or luciferin derivative, and one or more transferase quenching agents to a sample and detecting luminescence, wherein the activity of the reagent composition has enhanced stability [i.e., the reagent composition is capable of maintaining at least about 30%, more preferably at least about 60% activity (as measured by luminescence when the reagent composition is combined with the sample) for at least one hour, even more preferably at least 70%, 80%, 90%, 95%, 99% or greater activity for at least one hour, still more preferably for at least two hours and even more preferably for at least four hours relative to the reagent composition's activity when it is created, i.e., just after (0 to 10 minutes)], the luciferase enzyme is combined with a transferase quenching agent, and wherein the transferase quenching agent is present in the reagent composition at a concentration sufficient to reduce transferase activity endogenous to the sample by at least about 25%, more preferably at least about 30%, more preferably at least about 40%, even more preferably 50%, 60%, 70%, 80%, 90%, 95%, or 99% or greater relative to the sample's transferase activity in the absence of the transferase quenching agent. The reagent composition may be admixed before use by adding a solution comprising one or more transferase quenching agents to a lyophilized luciferase.

Loss of stability is defined as irreversible loss of activity. The reagent composition loses stability over time and the amount of activity lost varies depending on the particular luciferase, transferase quenching agent and, when present, enzyme stabilizing agent used. Preferably the stability of the reagent composition is demonstrable in the temperature range of about 20° C. to about 37° C. Although the methods of the invention may be used with a sample containing any amount of ATP, it is preferable to use a sample containing a non-saturated amount of ATP (i.e., a range where luminescence is linearly proportional to the concentration of ATP).

The luminescence generated by a luciferase reaction is typically detected with a luminometer although other detection means may be used. The presence of light greater than background level indicates the presence of ATP in the sample. The background level of luminescence is typically measured in the same matrix in which the sample exists, but in the absence of the sample. Suitable control reactions are readily designed by one of skill in the art. Preferred luciferases used in the compositions and methods of the invention generate a stable signal, i.e., they yield enhanced duration of luminescence in a luciferase reaction defined as less than 50% loss of luminescence per hour relative to the luminescence at the time the luciferase reaction was initiated. Preferred luciferases of the invention allow for multiple analyses of a sample over time or analysis of many samples over time, one hour after the luciferase is combined with the transferase quenching agent, more preferably two hours and most preferably four hours or more. Optionally, the luciferases used in the compositions and methods of the invention have enhanced thermostability properties.

Quantifying the amount of emitted light also quantifies the amount of ATP in a sample. Quantitation of ATP allows for quantitation of transferase activity. Quantitative ATP values are realized, for example, when the quantity of light emitted from a test sample is compared to the quantity of light emitted from a control sample or to a standard curve determined by using known amounts of ATP and the same luciferase, substrate, and reaction conditions (i.e. temperature, pH, etc.). It is understood that quantification involves subtraction of background values. Qualitative ATP values are realized when the luminescence emitted from one sample is compared to the luminescence emitted from another sample without a need to know the absolute amount of ATP present in the samples, e.g., a comparison of samples in the presence or absence of a test compound. Many such experiments can readily be designed by one of ordinary skill in the art.

Examples of transferase quenching agents include detergents, preferably detergents with charged groups such as cationic detergents [e.g., DTAB (dodecyltrimethylammonium bromide), CTAB (cetyltrimethylammonium) and BDDABr (benzyldimethyldodecylammonium bromide)], anionic detergents (e.g., SDS and deoxycholate), and zwitterionic detergents (e.g., sulfobetaine 3-10). To facilitate the method, a substrate for the luciferase, such as luciferin, may be included in the reagent composition. Other embodiments of the reagent composition further comprise transferase inhibitors such as NaF, vanadate and paranitrophenylphosphate. Still other embodiments of the reagent composition further comprise a buffer and magnesium. One of skill in the art knows that other cations, such as manganese and calcium, may be suitable substitutes for magnesium.

The reaction composition may also comprise an enzyme stabilizing agent. The enzyme stabilizing agent can be any compound that stablizes the luciferase from degradation. Suitable enzyme stabilizing agents include proteins (such as bovine serum albumin or gelatin) or detergents (preferably non-ionic detergents, most preferably THESIT). Additional examples of enzyme stabilizing agents are described in U.S. Provisional application No. 60/447,334, filed Feb. 13, 2003, entitled IMPROVED LUCIFERASE-BASED ASSAYS, which is incorporated by reference in its entirety.

Further, the present invention is useful for determining the effect of small molecules (including organic and inorganic molecules and synthetic and naturally occurring molecules) on transferase activity, which in turn allows the assement of whether the small molecule may function as a pharmaceutical drug. Thus, the invention is also directed to methods that determine the effect of a compound on a first sample containing transferase enzyme by contacting the first sample with a concentration of the compound and then at a later time contacting the first sample with the reagent composition of the invention, detecting and comparing the amount of luminescence in the first sample to an amount of luminescence in a second sample containing transferase. The second sample may be contacted with a concentration of the compound that is less than the concentration contacting the first sample with no compound. A lesser amount of luminescence detected from the first sample compared to the second sample may indicate that the compound comprises an inhibitory agent. In this way, inhibitory reagents may be discovered. Similarly, the invention is useful for discovering enzyme activity enhancing reagents, i.e., compounds that enhance transferase activity. Using the above example, a lesser amount of luminescence detected from the second sample compared to the first sample may indicate that the compound comprises a transferase enhancement agent. The invention is useful for comparing the effects of different compounds at the same concentration on transferase activity. The invention is also useful for comparing the effect of a compound on different types of transferases. One of skill in the art may develop many other such assays for which the invention is useful.

The invention also assembles the elements of the invention into kits. Such kits are designed to detect and quantitate transferase activity in a sample or determining the effects of compounds on transferase activity. Kits can be multifunctional such that more than one purpose can be realized. In one embodiment, a kit that is used to detect transferase activity in a sample may comprise lyophilized luciferase in one container, while another container contains reconstitution buffer with one or more transferase quenching agents. The transferase quenching agents may be non-detergent transferase inhibitors or detergents, preferably detergents with ionic groups including cationic detergents (preferably DTAB or BDDABr), anionic detergents (preferably SDS or deoxycholate) or zwitterionic detergents (preferably sulfobetaine 3-10) or a combination thereof.

The kit may also supply a luciferase substrate, such as luciferin. The kit may also supply magnesium or other cations such as manganese or calcium. To facilitate the use of control experiments with known concentrations of ATP, such as in embodiments of the kits that are used to quantify ATP in a sample, a container that has ATP may also be supplied in such kits. The kit may also supply a compound that quenches transferase activity in the sample (e.g., NaF). The kit may also supply an enzyme stabilizing agent, e.g., BSA or gelatin or THESIT. The kit may also supply one or more transferase enzymes such as kinases, transferase substrates and phosphate group donors (e.g., ATP) and optional buffers to support the transferase reaction.

A preferred embodiment of the kit contains components which, when combined, generate a reagent composition that (i) maintains at least about 30% (preferably at least about 60%, even more preferably at least 70%, 80%, 90%, 95%, 99%) activity for at least about one hour (preferably at least two hours, more preferably four hours), as detected by luminescence when the reagent composition is combined with a sample, and relative to the reagent composition's activity just after it is assembled (i.e., 0 to 10 minutes after the component comprising luciferase is combined with the component comprising a transferase quenching agent) and (ii) reduces at least about 25% or at least about 30%, (preferably at least about 40%, even more preferably at least about 50%, 60%, 70%, 80%, 90%, 95%, 99% or any increment therein) of the transferase activity that is endogenous to the sample relative to the sample's transferase activity in the absence of the transferase quenching agent.

The component comprising a transferase quenching agent may comprise more than one transferase quenching agent wherein they are present in the reagent composition at a concentration such that their combined effect reduces at least about 25% or at least about 30%, (preferably at least about 40%, even more preferably at least about 50%, 60%, 70%, 80%, 90%, 95%, 99% or any increment therein) of the transferase activity that is endogenous to the sample relative to the sample's transferase activity in the absence of the transferase quenching agent.

Most preferably the kit comprises a container comprising a buffered detergent solution, said buffered detergent solution at a pH in the range of about pH 6.0 to about pH 8.0, and said buffered detergent solution comprising DTAB whose concentration in the reagent composition is in the range of about 0.05% to about 2% (w/v) and optionally comprising NaF whose concentration in the reagent composition is in the range of about 1 mM to about 20 mM and optionally comprising THESIT whose concentration in the reagent composition is in the range of about 1% to about 5%. The kit additionally comprises a separate container comprising lyophilized luciferase, preferably a luciferase with the sequence of SEQ ID Nos: 1, 2, 3, or 4, most preferably SEQ ID Nos: 2 or 4. Preferably the luciferase, when combined with the buffered detergent solution creating the reagent composition, is at a concentration of 1 µg/ml or greater, more preferably at a concentration of 80 µg/ml or greater. Preferably, the container comprising lyophilized luciferase further comprises lyophilized luciferin. Optionally, the kit further comprises instructions for use of the kit for the purpose of measuring ATP.

BRIEF DESCRIPTION OF THE DRAWINGS

FIG. 1 illustrates the results of a protein kinase C ("PKC") titration study in a 96 Well Plate (n=2) according to the present invention.

FIG. 2 illustrates the results of Lck titration study in a 96 Well Plate (n=2) according to the present invention.

FIG. 3 illustrates the results of PKA titration study in a 96 Well Plate (n=8) according to the present invention.

FIG. 4 illustrates the results of a Staurosporine induced inhibition study of PKA according to the present invention.

DETAILED DESCRIPTION OF THE INVENTION

Figure 5:
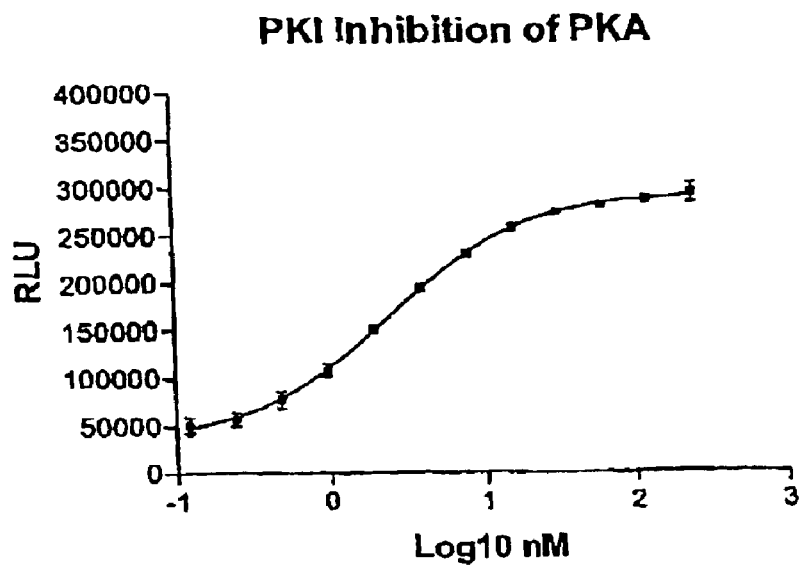
FIG. 5 illustrates the results of a cAMP-Dependent Protein Kinase Peptide Inhibitor ("PKI") induced inhibition of PKA in a 96 well plate (n=4) according to the present invention.

The present invention provides compositions with properties of enhanced stability comprising a luciferase, a luciferase substrate, and one or more transferase quenching agents. The invention further provides methods using these novel compositions to measure transferase activity in a sample by detecting ATP by reducing the steps of inhibition of transferase and addition of luciferase and substrate to a single step that is then followed by detection of the resulting luminescence. Preferably the luminescence resulting from the combination of a composition of the invention with a sample has an extended duration, i.e., dimished by less than about 50% per hour relative to the luminescence just after the composition is combined with the sample. The process of the invention significantly reduces the time and effort of luciferase-mediated detection of transferase activity in a sample by eliminating the need to separately inhibit transferase activity before adding luciferase.

There are multiple variations of kinase detection methods currently used, all of which act in a stepwise manner. Some such methods inactivate the transferase activity endogenous to a sample (e.g., by increasing sample pH), and then neutralize the transferase quenching agent, thereby converting the environment of the sample from one favoring transferase inhibition and unfavorable to luciferase activity to one favorable to luciferase activity prior to adding luciferase and measuring luminescence. Similar methods exist in which the environment of the sample is converted to one favoring luciferase activity at the same time that the luciferase enzyme is added. There are no ATP detection systems that provide a composition or method capable of inactivating endogenous transferase activity and allowing for luciferase activity in the same environmental milieu. And there are no ATP detection systems that provide a composition or method capable of lysing cells or extracting cellular ATP, inhibiting transferase activity endogenous to a sample and allowing for luciferase activity in the same environment. Therefore, current assays that use luminescence to detect ATP are handicapped by the need for successive, time-consuming steps.

In preferred embodiments, the present invention reduces to a single step the manipulations needed for measuring kinase activity in a sample, prior to luminescence measurement. In the single-step method of the invention, all of the necessary components of the ATP-dependent bioluminescence generating enzyme (e.g., luciferase), such as the bioluminescence generating enzyme, luminogenic substrate, and transferase quenching agent are comprised within a reagent composition and are added to a sample at once. In some embodiments, a component of the reagent composition is an enzyme stabilizing agent.

A. Definitions

Unless defined otherwise, all technical and scientific terms have the same meaning as is commonly understood by one of skill in the art to which this invention belongs. All cited patents and publications are incorporated by reference in their entirety unless otherwise noted.

The nomenclature recommendations of Demerec et al., 1966, where these are relevant to genetics, are adapted herein. To distinguish between genes (and related nucleic acids) and the proteins that they encode, the abbreviations for genes are indicated by italicized (or underlined) text while abbreviations for the proteins start with a capital letter and are not italicized. Thus, luc or Luc refers to the luciferase nucleotide sequence that encodes luciferase polypeptide or Luc.

An "isolated" or "purified" luciferase is one that has been identified and separated and/or recovered from a component of its natural environment.

The term "sample" as used herein, is used in its broadest sense. A sample is a composition suspected of transferase activity that is analyzed using the invention. While often a sample is known to contain or suspected of containing transferase activity, optionally in a growth media, or a cell lysate, a sample may also be a solid surface, (e.g., a swab, membrane, filter, particle), suspected of containing transferase activity. It is contemplated that for such a solid sample, an aqueous sample is made by adding the solid to the reagent composition of the invention or to another aqueous solution to which the reagent composition of the invention is added.

The term "detection," as used herein, refers to quantitatively or qualitatively determining the presence or absence of a component within the sample.

"Percent (%) amino acid sequence identity" is defined as the percentage of amino acid residues in one sequence that are identical to, with, or against amino acid residues in a second sequence in the region of overlap when the two sequences are optimally aligned. To determine percent amino acid identity, sequences are locally aligned and if necessary, gaps are introduced to achieve the maximum percent sequence identity; conservative substitutions are not counted when calculating sequence identity. Amino acid sequence alignment procedures to determine percent identity are well known to those of skill in the art. Publicly available computer software such as BLAST software (NCBI website) may be used to align peptide sequences. Those skilled in the art can determine appropriate algorithms and parameters for measuring alignment, including any algorithms and parameters needed to achieve optimal alignment of two amino acid sequences.

When amino acid sequences are aligned, the percent amino acid sequence identity of a given amino acid sequence A to, with, or against a given amino acid sequence B (which can alternatively be phrased as a given amino acid sequence A that has or comprises a certain percent amino acid sequence identity to, with, or against a given amino acid sequence B) can be calculated as:

$$\text{\% amino acid sequence identity} = (X/Y) \cdot 100$$

where X is the number of amino acid residues scored as identical matches in the optimal alignment of A and B by the sequence alignment program or algorithm and Y is the total number of amino acid positions aligned.

The term "luminescent", as used herein, includes bio-luminescence (i.e light produced by a living organism), chemiluminescence (light produced when a chemical reaction proceeds), and electrochemical-luminescence. When the enzyme involved has evolved in an organism by natural selection for the purpose of generating light, or the enzyme involved is a mutated derivative of such an enzyme, the luminescent reactions are also called "bioluminescent reactions" and the enzyme involved is also called a "bioluminescent enzyme." Examples of bioluminescent enzymes include, without limitation, firefly luciferase, Renilla luciferase, Cypridina luciferase, Aequorin photoprotein, Obelin photoprotein, and the like.

The term "luminogenic molecule" as used herein refers to a molecule capable of creating light via a chemical or biochemical reaction (e.g. luciferin, coelenterazine, or a functional analog thereof). Generally, a luminogenic molecule is either a high energy molecular species (e.g. a stabilized dioxetane), or it is transformed into a high energy molecular species by a chemical reaction. The chemical reaction is usually oxidation by oxygen, superoxide, or peroxide. In each case, the energy within the luminogenic molecule is released by the chemical reaction. Although at least some of this energy is released as photons of light, the energy can also be released in other forms, such as heat. The luminogenic molecules that do not yield light disperse their energy through alternative modes, often termed "dark pathways".

The term "luciferin derivative" as used herein refers to a type of luminogenic molecule or compound having a substantial structure of D-luciferin and is a luciferase substrate.

The term "transferase" as used herein refers to an enzyme that catalyzes the transfer or removal of a chemical entity or group such as a phosphate, acetyl, or methyl group from one molecule to another.

The term "transferase quenching agent" refers to a molecule, compound, or substance that is capable of substantially reducing or stopping transferase enzyme activity in a sample by any mechanism including, without limitation, direct or indirect inactivation, inhibition, denaturation, or sequestering.

B. Reagent Composition

The reagent composition of the present invention comprises one or more transferase quenching agents, preferably a detergent, and a non-endogenous ATP-dependent bioluminescence generating enzyme, wherein the composition is capable of maintaining at least about 30% enzymatic activity for at least about one hour, preferably at least about 2 hours, more preferably at least about 4 hours, compared to its activity just after (0 to 10 minutes) the enzyme is combined with the transferase quenching agent, and wherein the one or more transferase quenching agents are present in the composition at a concentration sufficient to collectively reduce transferase activity endogenous to the sample by at least about 25%, more preferably at least about 30%, 40%, 50%, 60%, 70%, 80%, 90%, 95% or 99% or any increment therein relative to the transferase activity endogenous to the sample in the absence of the transferase quenching agent. In preferred embodiments of the invention, the non-endogenous ATP-dependent enzymes are luciferases.

1. Luciferases

Luciferase enzymes whose catalytic products include light, offer sensitivity, a detectable product, and enable easy measurement of ATP. However, any luminescence-producing enzyme that is ATP-dependent may be used in the methods and compositions of the present invention.

At their most basic level, luciferases are defined by their ability to produce luminescence. More specifically, a luciferase is an enzyme that catalyzes the oxidation of a substrate, luciferin, thereby producing oxiluciferin and photons.

To date, five classes of luciferases have been identified (Jones et al., 1999; Thomson et al., 1997). Of these, beetle luciferases, such as that of the common firefly (family Lampyridae), form a distinct class with unique evolutionary origins (McElroy et al., 1969; White et al., 1969; White et al., 1975). Beetle luciferases are often referred to as firefly luciferases in the literature; however, firefly luciferases are actually a subgroup of the beetle luciferase class. Beetle luciferases may be purified from the lanterns of the beetles themselves or from protein expression systems well known in the art (Baldwin and Green, 2000; Beny and Dolivo, 1976; Branchini et al., 1980; Filippova et al., 1989).

Beetle luciferases, particularly firefly luciferase from the North American firefly *Photinus pyralis*, are well known in the art. The *P. pyralis* luciferase (LucPpy) consists of approximately 550 amino acids of $M_r$ 61 kDa as calculated by the protein encoded by the nucleotide sequence of the gene. However, other firefly luciferases are desirable, such as *Photuris pennsylvanica* firely luciferase (LucPpe2; 545 amino acid residues; GenBank 2190534, (Ye et al., 1997)). Mutant luciferases derived from LucPpe2 (e.g., LucPpe2m78 (also known as 78-0B10), SEQ ID NO: 1; LucPpe2m90(also known as 90-1B5), SEQ ID NO:2; LucPpe2m133 (also known as 133-1B2), SEQ ID NO:3; LucPpe2m146 (also known as 146-1H2), SEQ ID NO:4 are preferred; however, any luciferase that meets the limitations setforth herein may be used in the composition, method and kits of the invention. The method of making LucPpe2m78, LucPpe2m90, LucPpe2m133, and LucPpe2m146 is disclosed in PCT/US99/30925.

Isolated and/or purified luciferases are typically used in the present invention. Contaminant components of its natural environment are materials that would typically interfere with diagnostic or therapeutic uses for the luciferase, and may include enzymes, hormones, and other proteinaceous or non-proteinaceous materials. One technique to ascertain purity is applying SDS-PAGE analysis under non-reducing or reducing conditions using Coomassie blue or silver stain. Isolated luciferase includes luciferase in situ within recombinant cells, since at least one component of the luciferase natural environment will not be present. Luciferases can be isolated from biological specimens that produce luciferase or from a cell that expresses an exogenous polynucleotide encoding a desired luciferase (e.g., a nucleotide encoding 78-0B10, 90-1B5, 133-1B2, or 146-1H2 (SEQ ID NOs: 5-8, respectively)). Such techniques are well known to those of skill in the art.

The naturally-occurring substrate for beetle luciferases is firefly luciferin, a polytherocyclic organic acid, D-(−)-2-(6'-hydroxy-2'-benzothiazolyl)-$\Delta^2$-thiazolin-4-carboxylic acid (luciferin). Luciferin may be isolated from nature (e.g. from fireflies) or synthesized. Synthetic luciferin can have the same structure as the naturally occurring luciferin or can be derivatized, so long as it functions analogously (Bowie et al., 1973; Branchini, 2000; Craig et al., 1991; Miska and Geiger, 1987; Yang and Thomason, 1993). Examples of derivatives of luciferin include D-luciferin methyl ester, D-luciferyl-L-phenylalanine, D-luciferyl-L-Nα-arginine, D-luciferin-O-sulphate and D-luciferin-O-phosphate (Miska and Geiger, 1987), esters of luciferases that are hydrolyzed or acted upon by esterases to luciferin by components in a sample (Craig et al., 1991; Yang and Thomason, 1993). Other examples of useful luciferin analogs include naphthyl- and quinolylluciferin, which emit light in the green and red light spectra respectively (Branchini et al., 1989). There are multiple commercial sources for luciferin (e.g., Promega Corp. Madison, Wis.; Molecular Probes, Eugene, Oreg.).

The beetle luciferase-catalyzed reaction that yields luminescence (the luciferase-luciferin reaction) involves firefly luciferin, adenosine triphosphate (ATP), magnesium, and molecular oxygen. In the initial reaction, the firefly luciferin and ATP react to form luciferyl adenylate with the elimination of inorganic pyrophosphate. The luciferyl adenylate remains tightly bound to the catalytic site of luciferase. When this form of the enzyme is exposed to molecular oxygen, the enzyme-bound luciferyl adenylate is oxidized to yield oxyluciferin in an electronically excited state. The excited oxidized luciferin emits light on returning to the ground state:

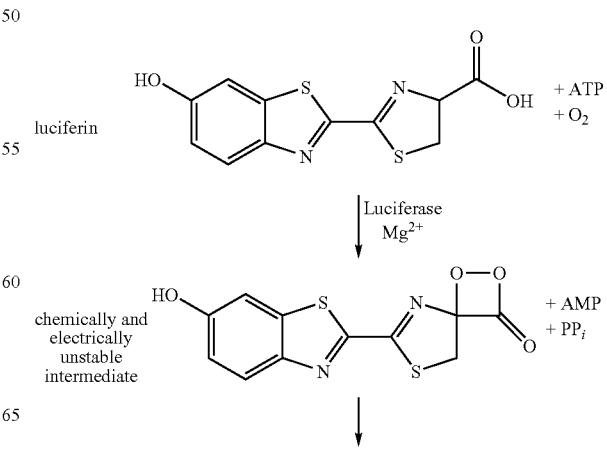

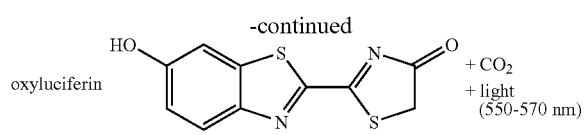

oxyluciferin → + $CO_2$ + light (550–570 nm)

It is contemplated that the ATP function of the reaction can be performed by an ATP analogue (e.g., dATP). It is also contemplated that other ions can serve as substitutes for magnesium ions (e.g., $Mn^{2+}$ or $Ca^{2+}$). Additionally, oxygen is a reactant of the reaction. Therefore, the reaction should not be conducted under anaerobic conditions. However, it is not generally necessary in practicing the invention to provide oxygen over and above that present in the air. Reactions can take place in closed vessels, provided there is sufficient oxygen in the reaction solution.

Most luciferase-luciferin reactions generate a flash of light that is short lived. However, some of the luciferases preferred for use with the invention, e.g., LucPpe2m146 and LucPpe2m90 luciferases, under the conditions of the invention generate a "glow-type" luminescent signal with less than 50% loss of luminescence per hour after the reagent composition is combined with the sample.

Any luciferase, luciferase variant, luciferase fragment, or variant luciferase fragment that retains the ability to generate luminescence when used in the reagent composition of the present invention and does not prevent the reagent composition from meeting the stability requirements of the present invention, can be used in the present invention.

A full length luciferase variant will have at least about 80% amino acid sequence identity, preferably at least about 81% amino acid sequence identity, more preferably at least about 82%, 83%, 84%, 85%, 86%, 87%, 88%, 89%, 90%, 91%, 92%, 93%, 94%, 95%, 96%, 97%, 98% amino acid sequence identity and most preferably at least about 99% amino acid sequence identity with a full-length native sequence luciferase sequence and retain the ability to generate luminescence. Ordinarily, variant luciferase fragments are at least about 50 amino acids in length, often at least about 60 amino acids in length, more often at least about 70, 80, 90, 100, 150, 200, 300, 400, 500 or 550 amino acids in length, or more and retain the ability to generate luminescence. A luciferase, luciferase fragment, luciferase variant or variant luciferase fragment may be fused to other non-luciferase amino acid sequences and still be functional in the invention.

Full length beetle luciferase, fragments of beetle luciferase, variants of beetle luciferase, and variant fragments of beetle luciferase enzyme used in the compositions and methods of the present invention may be purified from a native source or prepared by a number of techniques, including (1) chemical synthesis, (2) enzymatic (protease) digestion of luciferase, and (3) recombinant DNA methods. Chemical synthesis methods are well known in the art, as are methods that employ proteases to cleave specific sites. To produce segments of luciferase protein, segments of luciferase or luciferase variants can be made and then expressed in a host organism, such as E. coli. Methods such as endonuclease digestion or polymerase chain reaction (PCR) allow one of skill in the art to generate an unlimited supply of well-defined fragments. Preferably, luciferase fragments share at least one biological activity with native luciferase, as well as catalytic activity, although the level of activity may vary from that of the native luciferase.

Any type of amino acid substitution, insertion or deletion, or combination thereof may be used to generate a variant luciferase. However, a luciferase with a conservative amino acid substitution is more likely to retain activity. Useful conservative substitutions are shown in Table A "Preferred substitutions." Conservative substitutions whereby an amino acid of one class is replaced with another amino acid of the same type fall within the scope of the invention if the substitution does not impair luciferase activity.

TABLE A

Preferred substitutions

| Original residue | Exemplary substitutions | Preferred substitutions |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that effect (1) the structure of the polypeptide backbone, such as a β-sheet or α-helical conformation, (2) the charge or (3) hydrophobicity, or (4) the bulk of the side chain of the target site might modify luciferase function. Residues are divided into groups based on common side-chain properties as denoted in Table B. Non-conservative substitutions entail exchanging a member of one of these classes for another class.

TABLE B

Amino acid classes

| Class | Amino acids |
|---|---|
| Hydrophobic | Norleucine, Met, Ala, Val, Leu, Ile |
| neutral hydrophilic | Cys, Ser, Thr |
| Acidic | Asp, Glu |
| Basic | Asn, Gln, His, Lys, Arg |
| Disrupt chain conformation | Gly, Pro |
| Aromatic | Trp, Tyr, Phe |

Variant luciferase genes or gene fragments can be made using methods known in the art such as oligonucleotide-mediated (site-directed) mutagenesis, alanine scanning, and PCR mutagenesis. Site-directed mutagenesis (Carter, 1986; Zoller and Smith, 1987), cassette mutagenesis, restriction selection mutagenesis (Wells et al., 1985) or other known techniques can be performed on the cloned DNA to produce the luciferase variant DNA (Ausubel et al., 1987; Sambrook, 1989).

2. Preferred Luciferases

Preferred luciferases of the invention possess catalytic activity that depends on ATP and emits photons. Preferred luciferases of the invention have enhanced chemostability in the presence of transferase quenching agents relative to the level of the P. pyralis luciferase (LucPpy) chemostability in the same reaction conditions. Preferred luciferases used in the compositions and methods of the invention generate a stable signal, i.e., they yield enhanced duration of luminescence in a luciferase reaction defined as less than 50% loss of luminescence per hour relative to the luminescence at the time the luciferase reaction was initiated. Preferred luciferases of the invention allow for multiple analyses of a sample over time or analysis of many samples over time, one hour after the luciferase is combined with the transferase quenching agent, more preferably two hours and most preferably four hours or more. Optionally, the luciferases used in the compositions and methods of the invention have enhanced thermostability properties. An exemplified preferred luciferase is LucPpe2m146 (SEQ ID NO:4). Additional examples of enzymes useful in the invention include, but are not limited to, LucPpe2m78 (SEQ ID NO:1), LucPpe2m90 (SEQ ID NO:2), and LucPpe2m133 (SEQ ID NO:3).

The exemplified luciferases, LucPpe2m78 (SEQ ID NO:1), LucPpe2m90 (SEQ ID NO:2), LucPpe2m133 (SEQ ID NO:3) and LucPpe2m146 (SEQ ID NO:4) were generated from a mutant of $P.$ $pennsylvanica$ (T249M). The nucleic acid sequence encoding this protein was subjected to mutagenic methods including recursive mutagenesis followed by screens for thermostability, signal stability, and substrate binding and is fully described by Wood and Hall (WO 9914336, 1999).

Chemostability

"Chemostable luciferases" as used herein, defines luciferases that retain activity in the presence of compounds or conditions when those compounds or conditions typically inhibit transferases and disrupt the function of non-chemostable luciferases such as LucPpy. The above identified exemplary luciferases [(LucPpe2m78 (SEQ ID NO:1), LucPpe2m90 (SEQ ID NO:2), LucPpe2m133 (SEQ ID NO:3) and LucPpe2m146 (SEQ ID NO:4)] were found herein to have enhanced chemostability to transferase quenching agents.

Thus, preferred luciferases include those which maintain at least about 30% (preferably at least about 60%, 70%, 80%, 90%, 95%, 99%) enzymatic activity as measured by luminescence at least one hour (preferably at least two hours, more preferably at least four hours) after contact with an amount of transferase quenching agent, preferably a detergent, e.g., cationic detergent (preferably DTAB or BDDABr), anionic detergent (preferably deoxycholate or SDS) or zwitterionic detergent (preferably sulfobetaine 3-10) or combination thereof sufficient to collectively reduce transferase activity endogenous to a sample by at least about 25% (preferably at least about 30%, even more preferably at least about 40%, 50%, 60%, 70%, 80%, 90%, 95%, 99% or any increment therein) relative to the sample's transferase activity in the absence of the transferase quenching agent.

The chemostability of an enzyme also may be indicated by the rate of decline of its activity over time. For example, shortly (0 to 10 minutes) after mixing the transferase quenching agent and the luciferase, thereby creating the reagent composition, at several subsequent timepoints an aliquot of the reagent composition is added to a sample and relative light unit (rlu) measurements are obtained shortly thereafter. These measurements may be graphed to determine a trend of decline in enzyme activity in the reagent composition over time.

The preferred chemostable luciferases (e.g., Ppe2m78, Ppe2m90, Ppe2m133, and Ppe2m146) also retain activity in multi-detergent solutions. Specifically, solutions containing 0.01%, preferably 0.05%, 0.1%, 0.2%, 0.3%, 0.4%, 0.5%, 0.6%, 0.7%, 0.8%, 0.9%, most preferably 0.25% CHAPS (3-([3-Cholamidopropyl]dimethylammonio)-1-propane- sulfonate) with at least 0.01%, preferably 0.05%, 0.1%, 0.2%, and most preferably 0.3% or 1.0% BDDABr, taurocholic or taurolithocholic acids, or DTAB, or 0.01%, preferably 0.05%, 0.1%, 0.2%, 0.3%, 0.4%, 0.5%, 0.6%, 0.7%, 0.8%, 0.9%, most preferably 1.0% of taurocholic or taurolithocholic acids with at least 0.01%, preferably 0.05%, 0.1%, 0.2%, and most preferably 0.3% or 1.0% BDDABr, DTAB, or CHAPS. Other multi-detergent solutions in which LucPpe2m78, LucPpe2m90, LucPpe2m133 and LucPpe2m146 retain activity include 0.01%, preferably 0.05%, most preferably 0.1% TRITON X-100 with at least 0.01%, preferably 0.05%, 0.1%, 0.2%, 0.5%, most preferably 1.0% BDDABr, DTAB, or CHAPS; or 0.01%, preferably 0.05%, 0.1%, 0.2%, 0.3%, 0.4%, 0.5%, 0.6%, 0.7%, 0.8%, 0.9%, most preferably 1.0% of taurocholic or taurolithocholic acids with at least 0.01%, preferably 0.05%, 0.1%, 0.2% and most preferably 0.3 or 1.0% BDDABr, DTAB, or CHAPS; or 0.05%, 1.0%, 2.0%, 4.0%, preferably 2% polyethylene glycol 400 dodecyl ether (THESIT), with at least 0.05%, preferably 0.1%, 0.2% and most preferably 0.3% or 1.0% BDDABr, DTAB, or CHAPS.

Thermostability

In some embodiments, a thermostable luciferase that produces luminescence or other thermostable ATP-dependent enzyme that produces a detectable signal is desirable, especially in samples that are treated with heat immediately prior to ATP detection. A thermostable polypeptide remains active at temperatures that inactivate or denature other proteins. The LucPpe2m78, LucPpe2m90, LucPpe2m133 and LucPpe2m146 enzymes display increased thermostability compared to luciferases found in nature or encoded from polynucleotides isolated from nature.

Signal Stability

Preferred luciferases used in the compositions and methods of the invention generate a stable signal, i.e., such luciferases, when used in a luciferase reaction, yield luminescence with enhanced duration defined as less than 50% loss of luminescence per hour relative to the luminescence at the time the luciferase reaction was initiated. This property is referred to as signal stability. Preferred luciferases of the invention allow for multiple analyses of a sample over time or analysis of many samples over time, at least one hour after the luciferase is combined with the transferase quenching agent, more preferably at least two hours and most preferably at least four hours or more. The combination of a luciferase and a transferase quenching agent in the reagent composition, wherein the luciferase is capable of producing luminescence with enhanced duration while in the presence of a transferase quenching agent (and, optionally, kinase inhibitors) that stabilizes the amount of ATP present in the sample results in a reliable and efficient method for detecting and quantifying ATP for extended periods of time.

3. Other Desirable Luciferases

Any luciferase, luciferase fragment, or variants thereof that, in an ATP-dependent manner, emits photons upon oxidation of a substrate and is chemostable, i.e., retains activity in the presence of the transferase quenching agents of the invention, may be used in the present invention. Other desirable characteristics, although not obligatory, such as thermostability and signal stability, are contemplated. In addition, the luciferase may be fused to another amino acid sequence and still be functional in the present invenition. Such enzymes may be synthesized in vitro or isolated from other organisms.

Other luciferases are found in bacteria, unicellular algae, coelenterates, beetles (other than $P.$ $pennsylvanica$), fishes, and other organisms. Chemically, all luciferases involve exergonic reactions of molecular oxygen with different luciferins, resulting in photon production (Hastings, 1996; Hastings and Wilson, 1976; Wilson and Hastings, 1998; Wood et al., 1989). Preferably, other luciferases should be dependent on ATP for oxidation of luciferin, or the reaction conditions manipulated such that bioluminescence generation depends on ATP. One of skill in the art can ascertain ATP dependence for the luciferase-luciferin reaction.

The use of a luciferase other than that from beetles requires an appropriate luciferin molecule that upon oxidation generates a chemically and electrically unstable intermediate or a detectable enzymatic product. Other substrates may be used, as well as other ATP-dependent enzymes that produce a detectable enzymatic product. Detectable products include photons, radioactively-labeled products, insoluble or soluble chromogens, or other products that can be detected visually or through the use of devices.

C. Kits

When the invention is supplied as a kit, the different components of the composition may be packaged in separate containers and admixed prior to use. Such separate packaging of the components permits long-term storage without loss of luciferase-luciferin activity. However, when the various parts of the kit are admixed, thereby forming the "reagent composition", the reagent composition comprises a luciferase, such as exemplified by, but not limited to, SEQ ID NOs:1-4, and one or more transferase quenching agents wherein the activity of the reagent composition has enhanced stability [i.e., the reagent composition is capable of maintaining at least about 30%, more preferably at least about 60% activity for at least one hour, even more preferably at least 70%, 80%, 90%, 95%, 99% or greater activity for at least one hour, still more preferably for at least two hours and even more preferably for at least four hours (as measured by luminescence when the reagent composition is combined with a sample) relative to the reagent composition's activity when it is first created, i.e., 0 to 10 minutes after the luciferase enzyme is first combined with a transferase quenching agent], and wherein the transferase quenching agent is present in the reagent composition at a concentration sufficient to reduce transferase activity endogenous to a sample by at least about 25%, more preferably at least about 30%, even more preferably at least about 40%, 50%, 60%, 70%, 80%, 90%, 95%, or 99% or greater relative to the transferase activity in the absence of the transferase quenching agent. Instructional materials may also be enclosed in the kit, as well as materials that may act as standards or controls, depending on the purpose of the kit.

1. The Reagent Composition

In a preferred embodiment, the components of the reagent composition of the invention can be supplied as two parts that are admixed shortly before use: (1) a part comprising luciferase and (2) a part comprising one or more transferase quenching agents. An example of such an embodiment is represented in Table C and others are represented in the Examples. The luciferase component may further comprise luciferin and preferably is lyophilized. The luciferase component optionally comprises excipients for lyophilization, protein (luciferase) stabilizer, magnesium (or alternative cation), and a magnesium chelator (or alternative cation chelator). The transferase quenching agent component may further comprise a buffer, divalent cation metal chelators, magnesium (or alternative cation), a defoaming agent, and an enzyme stabilizer (e.g., THESIT). The different components of the invention may comprise subsets of these parts and may be combined in any way that either facilitates the application of the invention or prolongs storage life.

TABLE C

Preferred components of a kit

| Component | Action | Preferred embodiments |
| --- | --- | --- |
| luciferase\ luciferin | Catalyzes luciferase-luciferin reaction in one step | Ppe2m90 or Ppe2m146 luciferase |
| | Substrate | Luciferin |
| | Lyophilization excipient and protein stabilizer | Highly purified porcine dermal collagen (Prionex) |
| | Enzyme cofactor | $MgSO_4$ |
| | Chelates Mg after ATP removal | 1,2-Cyclohexanediaminetetraacetic acid (CDTA) |
| Transferase quenching agent/ buffer | Buffer | Citrate buffer Potassium Phosphate buffer |
| | Buffer | 2-(N-Morpholino)ethanesulfonic acid (MES) |
| | Chelates divalent metal cations | Ethylenediaminetetraacetic acid (EDTA) |
| | Defoamer | MAZU DF204 |
| | transferase quenching agent | DTAB |
| | Transferase quenching agent | NaF |
| | Non-ionic detergent enzyme stabilizer | THESIT, Polyoxyethylene(9)-lauryl-ether |

2. Luciferase-luciferin Component

All luciferases, luciferase variants, luciferase fragments and variant luciferase fragments that catalyze an ATP-dependent reaction and generate luminescence are contemplated for use in the invention. Some embodiments eliminate the luciferin; for example, allowing a user to supply a luciferin of his/her choice, or the luciferin may be provided separately. The type of luciferin provided may vary but it must be a substrate for the type of luciferase provided.

In one embodiment, a kit supplies the luciferase as an anhydrous preparation. Anhydrous preparations of luciferase may be lyophilized, in which water is removed under vacuum, freeze-dried, crystallized, or any other method that removes water that does not inactivate luciferase. Excipients that bulk the preparation and stabilize luciferase, such as serum albumins or Prionex, may also be included. In other embodiments, luciferase may be suspended in an aqueous composition comprising glycerol or other solvent in which the enzyme is stable. The skilled artisan can easily determine the amounts of the various constituents that work in the compositions and methods of the invention.

3. Transferase Quenching Agent Component

In a preferred embodiment, the kit comprises a component containing one or more transferase quenching agents within a solution optionally containing other functional components, such as buffers, defoamers, enzyme stabilizers, and the like. This component may be supplied as a working solution or as a concentrate. The transferase quenching agent may be any of those described herein above. This component may further comprise agents that chelate metal ions that may interfere with the luciferase-luciferin reaction (e.g. EDTA, EGTA), magnesium (preferably supplied as a salt, such as sulfate or chloride; or other functionally equivalent cation), defoaming agents, and inhibitors of ATP generating enzyme (e.g. NaF). Buffers that maintain pH of the working solution, e.g. citrate or MES (which may be supplied as a salt, such as sodium or free acid or base) or any other appropriate buffer may be used.

Transferase Quenching Agent

One aspect of the invention is a transferase quenching agent, preferably a detergent that inhibits transferases, more preferably a detergent with a charged group, e.g., cationic detergent (preferably DTAB or BDDABr), anionic detergent (preferably deoxycholate or SDS) or zwitterionic detergent (preferably sulfobetaine 3-10). Such inhibitors prevent transferases endogenous to the sample from processing ATP to adenosine diphosphate (ADP) and adenosine monophosphate (AMP) before the luciferase is allowed to utilize the ATP in the sample for the luciferase-luciferin reaction. Transferase quenching agents may inactivate transferases directly or indirectly. They may bind to transferases, either in the active sites, thus preventing substrate binding, or denature transferases, such as by denaturing detergents, or they may selectively sequester transferases from their substrates.

One embodiment of the present invention uses cationic detergents such as DTAB or BDDABr detergents that act as transferase quenching agents. However, other transferase quenching agents are contemplated, such as other cationic detergents, anionic detergents (e.g., SDS and deoxycholate) and zwitterionic detergents (e.g., sulfobetaine 3-10).

For DTAB or BDDABr the concentration in the reagent composition is preferably in the range of about 0.02% to about 5.0%, more preferably about 0.05%, still more preferably about 0.1%, 0.2%, 0.3%, 0.4%, 0.5%, 0.6%, 0.7%, 0.8%, 0.9%, 1.0%, 1.1%, 1.2%, 1.3%, 1.4% and 1.5% and most preferably to a final concentration of about 1.0% in the reagent composition.

Other non-cationic detergent transferase quenching agents are contemplated for inclusion in the reagent composition; their requirements are that they, like DTAB, preferably inhibit at least about 25%, more preferably at least about 30%, 40%, 50%, 60%, 70%, 80%, 81%, 82%, 83%, 84%, 85%, 86%, 87%, 88%, 89%, 90%, more preferably at least about 91%, 92%, 93%, 94%, 95%, 96%, 97%, 98%, 99% and most preferably about 100% of endogenous transferase activity in a sample when present in a reagent composition wherein the reagent composition is capable of maintaining at least 30%, 40%, 50%, 60%, 70%, 80%, 81%, 82%, 83%, 84%, 85%, 86%, 87%, 88%, 89%, 90%, more preferably at least about 91%, 92%, 93%, 94%, 95%, 96%, 97%, 98%, 99% and most preferably about 100% activity, as measured by luminescence after the reagent composition is combined with the sample, for at least one hour, more preferably at least 2 hours compared to the reagent composition's activity just after the luciferase is combined with the transferase quenching agent. Potentially suitable non-cationic detergents that function as transferase quenching agents include anionic detergents (preferably SDS and deoxycholate), zwitterionic detergents (preferably sulfobetain 3-10). The concentration of a particular transferase quenching agent will vary depending on the inhibitor used, and to some extent, the sample being analyzed. One of skill in the art is familiar with methods to determine the appropriate concentration of a transferase quenching agent for inclusion in the reagent composition; for example, they may examine luciferin-luciferase derived signals over time, comparing those samples that have varying concentrations of a candidate transferase quenching agent to those samples containing no known transferase quenching agents.

Transferase quenching agents also include non-detergent inhibitors of transferase activity which may be used alone or in combination with detergents. An example of an effective inhibitor is NaF (Bostick et al., 1982). Such compositions comprise NaF at concentrations of at least 0.5 mM, preferably at least 1 mM, more preferably at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 mM or any increment therein; 2 mM is most preferred. Other inhibitors of ATP-generating enzymes include other kinase inhibitors, such as vanadate, AMP, DAPP (Bostick et al., 1982), dichloroacetic acid (Kiechle et al., 1980), staurosporine, UCN-01, and calphostin C (Tamaoki 1991). Generally, any suitable non-detergent inhibitor may be used as a transferase quenching agent and at any suitable concentration so long as it does not adversely affect luciferase so as to take it outside the utility of the invention. One of skill in the art will know how to determine the appropriate concentration of such an inhibitor, whether the inhibitor is novel or well-known.

It is fully anticipated that the most preferred concentration and even the concentration range for the transferase quenching agent functional in the methods of the invention will vary for different agents. For example, SDS detergent concentrations functional in the methods of the invention are about 0.002%. See, for instance, Examples 2 and 3, in U.S. patent application Ser. No. 09/813,279, filed Mar. 9, 2001, entitled METHOD FOR DETECTION OF ATP, published as U.S. Ser. No. 20030104507A1, which is incorporated by reference in its entirety. The functional concentration range for a detergent and/or non-detergent inhibitor used in the present invention may readily be determined by one of skill in the art using the methods disclosed herein.

It is contemplated that some transferase quenching agents, at some of the concentrations useful in the invention, may be insoluble or have low solubility in aqueous solutions. These compounds may first be dissolved in an organic solution (e.g., dimethyl sulfoxide or dimethylformamide) and then diluted into the reagent composition for use in the composition and methods of the invention.

Buffers

Any buffers that maintain suitable pH for the working solution and do not interfere with the luciferase-luciferin reaction are contemplated. The preferred pH range is between about pH 4.5 and about pH 9.0, more preferably between about pH 6.0 and about pH 8.0. In addition to MES and citrate buffers, other buffers, such as phosphate buffered saline (PBS), Tris, N-(2-Hydroxyethyl)piperazine-N'-(2-ethanesulfonic acid) (HEPES), piperazine-1,4-bis(2-ethanesulfonic acid) (PIPES), borate, and any other buffer known to those of skill in the art may be suitable. Selection of appropriate buffers depends on pH buffering capacity and interaction with the luciferase-luciferin reaction.

Defoamers

Defoaming agents are desirable to prevent foam from interfering with the detection of bioluminescence, especially in applications that quantify luminescence. Such agents as MAZU may be organic or silicone based. Selection of defoamers depends on their ability to eliminate foam without interfering with the luciferase-luciferin reaction.

Magnesium

The beetle luciferase-luciferin reaction is dependent not only on ATP, but also on magnesium ions. To assure luciferase activity, magnesium is exogenously supplied. In addition to magnesium sulfate, other salts of magnesium are contemplated, such as magnesium chloride, magnesium gluconate, magnesium acetate, magnesium bromide, magnesium carbonate, etc. In any case, the magnesium complex must dissociate to make $Mg^{2+}$ ions available to the luciferase and not interfere with the luciferase-luciferin reaction. One of skill in the art is aware that other cations may be functional in place of magnesium. These include calcium and manganese.

In some applications, endogenous magnesium should be sufficient in which cases exogenous magnesium could be eliminated.

Stabilizing Agents

While resistant to the action of nonionic and low concentrations of zwitterionic detergents (Simpson and Hammond, 1991), native firefly luciferase is inactivated by cationic detergents, such as benzalkonium chloride, benzethonium chloride, CTAB (cetyltrimethylammonium), DTAB (dodecyltrimethylammonium bromide), and methylbenzethonium chloride (Simpson and Hammond, 1991).

The stabilizing agent can be any compound that stablizes the luciferase from degradation. Suitable stabilizing agents include proteins (such as bovine serum albumin or gelatin) or detergents (preferably non-ionic detergents, most preferably THESIT).

Other Agents

Other agents that may be included in a kit include substances that are known to enhance the duration of luminescence resulting from a luciferase reaction, such as co-enzyme A (CoA), thiol reagents, such as dithiothreitol and β mercaptoethanol (Wood, U.S. Pat. No. 5,283,179, 1994; Wood, U.S. Pat. No. 5,650,289, 1997), metal ion chelators such as EDTA to prolong the signal and protease inhibitors (Scheirer, U.S. Pat. No. 5,618,682, 1997; Scheirer, U.S. Pat. No. 5,866,348, 1999), or high concentrations of salts (Van Lune and Trer Wiel, WO 00/18953, 2000).

Other Kit Contents

Kits may also include reagents in separate containers that facilitate the execution of a specific test, such as cell viability, cytotoxicity, cell proliferation, or determination of ATP concentration. For example, ATP may be supplied so that standard curves may be determined or to be used as internal controls. Substances that are known to be transferase inhibitors or activators can be included for use as a positive control in detection of transferase activity or for determining the effects of compounds on transferase activity. The kit may supply multiwell plates and/or one or more transferase enzymes. The kit may optionally include substrates for the transferases, buffer, and co-activators of the transferases.

4. Containers or Vessels

The reagents included in the kits can be supplied in containers of any sort such that the life of the different components are preserved, and are not adsorbed or altered by the materials of the container. For example, sealed glass ampules may contain lyophilized luciferase or buffer that have been packaged under a neutral, non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules, and envelopes, that may consist of foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

5. Instructional Materials

Kits may also be supplied with instructional materials. Instructions also may be printed on paper or other substrate, and/or may be supplied as an electronic-readable medium, such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail. In a preferred embodiment, the instructions instruct the user to combine the luciferase with the transferase quenching agent before adding the reagent composition to a sample.

D. Reagent Composition Activity

To measure luminescence and thereby determine the reagent composition activity, the relative light unit (rlu) value generated by the luciferase reaction at a timepoint of interest after the reagent composition is combined with a sample may be measured. For example, an rlu value may be obtained by measuring the resulting luminescence from a sample with a known concentration of ATP combined with the reagent composition just after (0-10 min) the component comprising the transferase quenching agent is added to the component comprising the luciferase thereby creating the reagent composition. This is considered 100% activity (time zero) under those conditions. If, after combining the component comprising the transferase quenching agent with the component comprising the luciferase and thereby generating the reagent composition, the reagent composition is left for two hours, preferably in the temperature range of room temperature (about 20° C.-about 25° C.) to about 37° C., prior to measuring luminescence under identical conditions as the time 0 assay, and the rlu value obtained is greater than 60% of that obtained at time 0, then the reagent composition retained at least 60% of its activity for two hours.

A reagent composition of the present invention retains 30%, 40%, 50%, 55%, 60%, 65%, 70%, 75%, 80%, 85%, 90%, 95%, 96%, 97%, 98%, 99% or any increment therein and most preferably 100% of its activity, as measured by luminescence after the reagent composition is combined with the sample for at least one hour, preferably for at least two hours, relative to its activity when formulated (time zero)— that is from the time the component comprising the transferase quenching agent was added to the component comprising luciferase or shortly thereafter (0-10 minutes).

In one preferred embodiment, the working stock of the reagent composition comprises DTAB or BDDBr in concentrations of about 0.02% (preferably about 0.05%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.5%, 3%, 3.5%, 4%, 4.5%, 5%, 5.5%, 6%, 6.5%, 7%, 7.5%, 8%, 8.5%, 9%, 9.5%, 10% and any increment therein, more preferably about 1%) and retains at least about 30% (preferably at least about 40%, 50%, 60%, 70%, 80%, 90%, 95%, 99%) of activity at least one hour (preferably at least two hours) after formulation.

In another preferred embodiment, the reagent compositions comprise sulfobetaine at a concentration of 0.6%, 0.7%, 0.8%, 0.9% or 1.0% or any increment therein, SDS at a concentration of 0.001%, 0.002%, 0.003%, 0.004% or 0.005% or any increment therein, or deoxycholate at a concentration of 0.1%, 0.2%, 0.3%, 0.4%, 0.5%, 0.6% or any increment therein and retain at least about 30% (preferably at least about 40%, 50%, 60%, 70%, 80%, 90%, 95%, 99%) of activity at least one hour (preferably at least two hours) after formulation.

E. Detecting and Quantifying the Products of the Luciferase-luciferin Reaction

A beetle luciferase-luciferin reaction results in the generation of light ("luminescence"). The invention provides assays for ATP measurement by measuring luminescence. Users may simply visually inspect sample reactions to ascertain the production of light. However, more sensitive instrumentations allow not only detection of faint signals, but also quantification of the light signal. Also contemplated are reactions in which non-light products are measured, according to the nature of the products. Any assay for measurement of ATP that results in a signal may benefit from the present invention. Appropriate instruments and methods for such products will be apparent to the skilled artisan.

In all cases in which light is detected, specialized instruments, such as luminometers, can read the light product of a luciferase-luciferin reaction. Any instrument that can detect light of the wavelengths emitted by the luciferase-luciferin reaction may be used. Such instruments may read samples singularly, or in high-throughput screens, may read many samples housed in the wells of a microwell plates (6, 24, 48, 96, 384, 1536 and so on, well formats). Clearly, the devices used to measure the emitted light do not limit the invention. Other devices that can be used include scintillation counters (Nguyen et al., 1988) or instruments invented or adapted to be sensitive to luminescence, such as photometers (Picciolo et al., 1977). Photographic film or X-ray film may also be used to detect luminescence. In addition, a user may visually inspect a sample to qualitatively evaluate luminescence.

F. Uses for ATP-dependent Luciferase-luciferin Reactions

Because the beetle luciferase-luciferin reaction is ATP-dependent, luciferase can be used to assay for ATP. The reaction is remarkably sensitive, allowing ATP to be detected in a sample containing as little as $10^{-16}$ moles ATP or less. This sensitivity can be exploited to understand cell viability and the effects that exogenous substances may exert on cell metabolism and viability. In a cellular context, ATP powers cellular metabolism, the presence of ATP correlates to an actively metabolizing cell, the cell is "viable".

The invention is drawn to methods, compositions and kits that are used to effectively and accurately detect and quantify cellular ATP levels, exploiting the ATP-dependence of beetle luciferase to oxidize luciferin.

The invention comprises the addition of a single composition (reagent composition) that comprises a luciferase and at least one transferase quenching agent to a sample and then detecting luminescence. Optionally, a kinase inhibitor or a compound that prevents accumulation of ATP can also be present in the reagent composition. Additionally, a cell-lysing agent (e.g., a polyoxyethylene such as THESIT) or an ATP extracting agent may be present in the composition. This single step comprising adding the reagent composition followed by reading the luminescence represents a significant advance in assays for ATP.

1. Detecting ATP

The methods, compositions and kits of the invention provide for the simple qualitative or quantitative detection of ATP (or ATP analogue which can function as a luciferase substrate) in a sample. In preferred embodiments, a simple qualitative experiment in which luminescence is generated in a sample using the invention, indicates the presence of ATP. Luminescence is generated using a reagent composition comprising luciferase such as LucPpe2m78, LucPpe2m90, LucPpe2m133 or LucPpe2m146, and one or more transferase quenching agents. In addition, the reagent composition may further comprise one or more of the following components: luciferin, which may be reconstituted from a lyophilized preparation, (alternatively, an appropriate luciferin-analogue substrate), transferase quenching agent(s), inhibitor(s) of ATP-consuming enzymes such as kinases, divalent cation (e.g. magnesium), enzyme stabilizing agent, buffer, cell-lysis agent, cellular ATP extracting agent, or exogenously added ATP.

A sample may be anything that is suspected of containing ATP or ATP analogue, such as cell lysates, intact cells, biopsies, foods, beverages, swabs wiped on surfaces such as those of animals, plants, or inanimate objects, and the like. Other examples of samples include compositions of a known ATP concentration. Cells or cell lysates may be from any organism, prokaryotic or eukaryotic. Examples of prokaryotic cells include *E. coli*, *P. aeruginosa*, *B. subtilis*, and *S. typhimurium*. Eukaryotic cells may be from plants, animals, fungi, insects, etc. or cultured cells from such organisms. Examples include *A. thaliana* and *Brassica* sp., *Chlamydomonas* sp. and *Volvox* sp. (plants), *H. sapiens* and *Mus* sp. (animals), *Saccharoymyces* sp. (esp. cerevisae and pombe) and *Neurospora* sp. (fungi), *D. melanogaster* and *C. elegans* (insects), in vitro cultured callus cells from any plant, primary cells cultured in vitro from any organism (such as organ explants from, for example, rodents), mammalian cell lines such as Madin-Darby canine kidney (MDCK) and Chinese hamster ovary (CHO) cells, and insect cell lines such as Z cells. These examples are furnished only as examples and are not meant to be limiting.

A cell lysate comprises cellular components that are no longer organized into a recognizable intact cellular architecture. Cell lysates may have soluble and insoluble components, either of which may be removed before using the lysate. Lysates may be prepared by any means, including physical disruption using sonication, a dounce, mortar and pestle, freeze-thaw cycling, or any other device or process that destroys the physical integrity of cells; or lysis by detergents, such as those in which LucPpe2m146 retains activity, such as zwitterionic and nonionic detergents, or cationic detergents DTAB or CTAB. Preferably, the cell lysate is produced in such a way that the integrity of the ATP concentration is preserved at the time the cells are harvested. To accurately detect ATP in a sample, enzymes that would degrade cellular ATP or those that would generate ATP are preferably inhibited. In the absence of such inhibitors, an inaccurate determination of ATP concentration risks being made. Inhibitors such as DTAB inactivate transferases, while other molecules such as NaF inactivate ATP-generating enzyme activity. It is hypothesized, yet not fully understood, that for those cell types in which NaF is effective (e.g., lymphoid cells), NaF is potentially acting to inhibit (a) kinase(s).

2. Quantifying ATP

The compositions, methods and kits of the invention permit a user to quantify the amount of ATP in a sample by quantifying the amount of luminescence. The invention is applied to a sample of interest, and also to samples containing known amounts of ATP (controls). The signal generated from applying the invention to a sample of unknown ATP concentration is correlated to signals generated either by internal controls (the addition of a known amount of ATP to a sample and measuring the subsequent luminescence) or external standard curves, generated by measuring the luminescence of several samples of known ATP concentrations and plotting them graphically. Such methods are known to skilled artisans. (Moyer and Henderson, 1983; Ronner et al., 1999; Stanley, 1989; Wood et al., 1989).

3. Effects of Compounds on Transferase Activity

The compositions, methods and kits of the present invention can be applied to measure the effects of compounds, such as inorganics, small organics, peptides, proteins and polypeptides, on transferase activity when contacted with a sample (Aiginger et al., 1980; Andreotti et al., 1995; Bradbury et al., 2000; Cree and Andreotti, 1997; Crouch et al., 1993; Kangas et al., 1984). Determining the effects of compounds on transferase activity can assess the measure of a potential pharmaceutical composition's effectiveness. Inhibitors of tranferase activity can be useful in the treatment of cancer cells, especially if they selectively kill quickly-dividing cells. In other cases, a compound with some other usefulness may be negated if a transferase inhibitor effect is not desired. These compounds may be catalogued in compound libraries, or tested singly. Such applications of the invention apply controls in which samples are contacted with control substances whose effects on transferase activity are known. Also preferably, controls include samples in which luciferase and the compound are present together to assure that the compound itself is not directly affecting luciferase activity.

The following examples are intended to illustrate the present invention without limitation.

EXAMPLES

Example 1

Determining the Activity of Lipid Dependent Serine/Threonine Kinases

Commercially available Protein Kinase C ("PKC") was titrated in a 96 well plate (n=2). Kinase reactions were performed in 20mM Tris-HCl (pH 7.5), 10 mM $MgCl_2$, 0.1 mg/ml bovine serum albumin ("BSA"), 250 µM EGTA, 400 µM $CaCl_2$, 0.32 mg/ml phosphatidylserine, 0.032 mg/ml diacylglycerol, 10 µM biotinylated peptide (AAKIQASFRGH-MARKK), and 1 µM ATP with the indicated amount of PKC (Promega, Catalog # V5621). Final kinase reaction volume was 50 µl. Following a 90 minute kinase reaction, 50 µl of a luminescent buffer reagent (pH 6.0+0.15) containing 20 mM citrate; 55 mM MES; 10.5 mM magnesium sulfate; 0.6 mM CDTA; 225 mM_potassium buffer (pH 6.0); 1 mM NaF; 0.0125 µM sodium pyrophosphate; 0.5% DTAB; 1.0% Thesit; 0.1% Mazu DF 204; 2.5 mM luciferin; and 0.2% 2-(N-morpholino) ethanesulfonic acid containing 10 µg/ml [TRUE?] of a thermostable firefly luciferase reporter 146-1H2 (see SEQ ID NO.: 4 and SEQ ID NO.: 8) was added to each well and allowed to incubate for 10 minutes prior to reading luminescence. FIG. 1 clearly shows that a reliable titration curve is obtained measuring the kinase activity of a serine/threonine kinase using a method of the present invention.

Example 2

Determining the Activity of Tyrosine Kinases

Commercially available Lck was titrated in a 96 well plate (n=2). Lck is a gene family encoding nonreceptor tyrosine kinases of the Src family. Kinase reactions were performed in 8 mM imidazole hydrochloride (pH 7.3), 8 mM β-glycerophosphate, 200 µM EGTA, 20 mM $MgCl_2$, 1 mM $MnCl_2$, 0.1 mg/ml BSA, 250 µM biotinylated peptide substrate (AEEEI YGELEA), and 3 µM ATP with the indicated amount of Lck (Upstate, Catalog # 14-442). Final kinase reaction volume was 50 µl. Following a 60 minute kinase reaction, 50 µl of a luminescent buffer reagent as described in Example 1 was added to each well and allowed to incubate for 10 minutes prior to reading luminescence. FIG. 2 clearly shows that a consistent titration curve is obtained using the method of the present invention.

Example 3

Determining the Activity of Cyclic-AMP Dependent Serine/Threonine Protein Kinase Commercially available Protein Kinase A ("PKA") was titrated in a 96 well plate (n=8). Kinase reactions were performed in 40 mM Tris-HCl (pH 7.5), 20 mM $MgCl_2$, 0.1 mg/ml BSA, 5 µM kemptide (LRRASLG), and 1 µM ATP with the indicated amount of PKA (Promega, Catalog # V5161). Final kinase reaction volume was 50 µl. Following a 20 minute kinase reaction, 50µl of a luminescent buffer reagent as described in Example 1 was added to each well and allowed to incubate for 10 minutes prior to reading luminescence. FIG. 3 clearly shows that using the method of the present invention, a reliable titration curve is obtained.

Example 4

Determining the Inhibition of Protein Kinase A Induced by Staurosporine

Inhibition of commercially available PKA in a 96 well plate (n=4) was induced by Staurosporine. Kinase reactions were performed in 40 mM Tris-HCl (pH 7.5), 20 mM $MgCl_2$, 0.1 mg/ml BSA, 5µM kemptide (LRRASLG), and 1 µM ATP with the indicated amount of Staurosporine (Calbiochem, Catalog # 569397) shown in FIG. 4. Final kinase reaction volume was 50 µl. Following a 20 minute kinase reaction, 50 µl of the luminescent buffer agent described in Example 1 was added to each well and allowed to incubate for 10 minutes prior to reading luminescence. FIG. 4 shows that using the method of the present invention, an $IC_{50}$ can be easily and reliably obtained. Moreover, the $IC_{50}$ value determined by the present invention is consistent with those obtained using well established assays for protein kinase inhibition.

Example 5

Determining the Inhibition of Protein Kinase A Induced by PKI cAMP-Dependent Protein Kinase Peptide Inhibitor (PKI) induced inhibition of PKA in a 96 well plate (n=4). Kinase reactions were performed in 40 mM Tris-HCl (pH 7.5), 20 mM $MgCl_2$, 0.1 mg/ml BSA, 5 µM kemptide (LRRASLG), and 1 µM ATP with indicated amount of PKI (Promega, Catalog # V5681). Final kinase reaction volume was 50 µl. 0.5 U/well of PKA was utilized in the reaction. Following a 20 minute kinase reaction, 50 µl of the luminescent buffer reagent of Example 1 was added to each well and allowed to incubate for 10 minutes prior to reading luminescence. FIG. 5 shows that the $IC_{50}$ can be easily and reliably obtained using the method of the present the invention. Moreover, the $IC_{50}$ measured using the present invention is consistent with those obtained using well-established assays for protein kinase inhibition.

Example 6

Z' Analysis of Kinase Assay of the Present Invention

Figure 6:
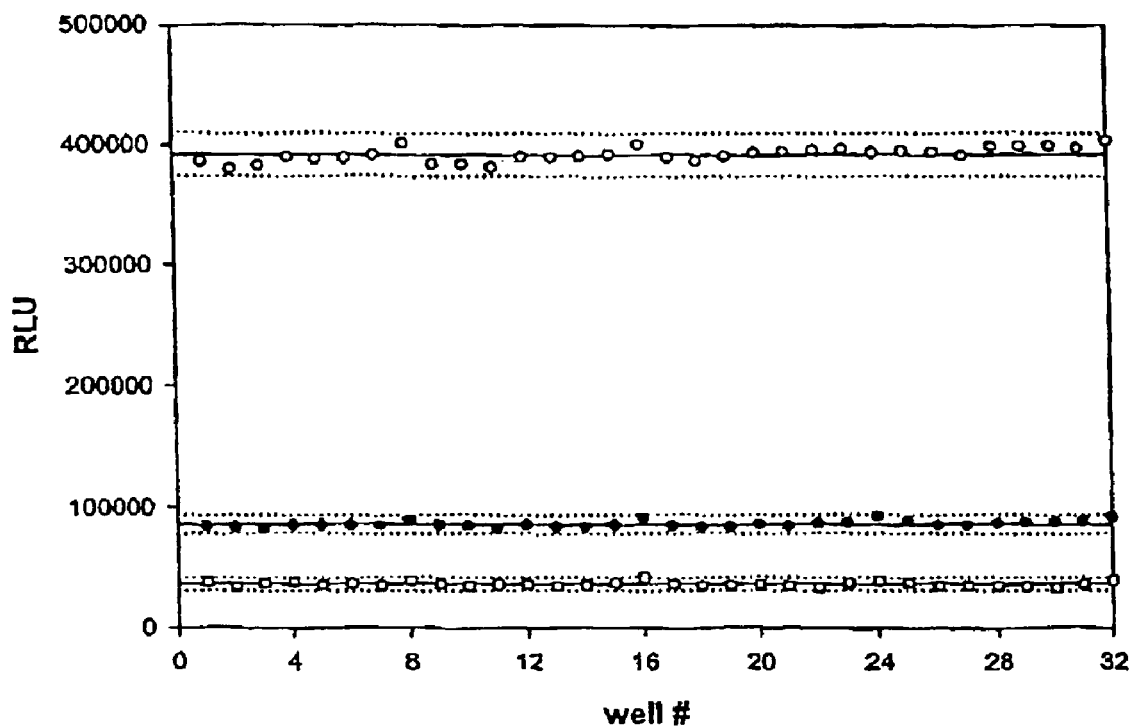
FIG. 6 shows a Z' analysis of Protein Kinase Activity using PKA in a 96 well plate (n=32) according to the present invention.

The assays of the present invention can be readily used in high throughput screening using multi-well plates. A common indicator of the reproducibility and effectiveness of an assay is a z' factor or analysis. An accepted z' value is typically ≧0.5. In the present example, Z' analysis of PKA Assay in a 96 well plate (n=32) was conducted. Kinase reactions were performed in 40 mM Tris-HCl (pH 7.5), 20 mM $MgCl_2$, 0.1 mg/ml BSA, 5 µM kemptide (LRRASLG), and 1 µM ATP with either no PKA (open circles), 0.25 U/well PKA (closed circles), or 0.5 U/well PKA (open squares). "U/well" is units of kinase per well. Final kinase reaction volume was 50 µl. Following a 20 minute kinase reaction, 50 µl of the luminescent buffer reagent of Example 1 was added to each well and allowed to incubate for 10 minutes prior to reading luminescence. Solid lines are the mean and dotted lines are the mean ±3SD of the respective data sets. Z' values were 0.93 for 0.5 U/well PKA and 0.92 for 0.25 U/well PKA. FIG. 6 clearly shows the reproducibility of the assay of the present invention.

Example 7

Determining the Utility of the Invention in Identifying Inhibitors in a High Through Put Screen In order to further demonstrate the usefulness of the present invention as a high throughput screen, eight (80) compounds from the LOPAC Library of Pharmacologically Active Compounds for Assay Validation and High Throughput Screening (Sigma, Catalog #SC001) were included on a 96 well plate. Kinase reactions were performed in 40 mM Tris-HCl (pH 7.5), 20 mM $MgCl_2$, 0.1 mg/ml BSA, 5 µM kemptide (LRRASLG), 1 µM ATP, and 0.5 U/well PKA in the presence of 10 µM of each library compound. The final kinase reaction volume was 50 µl. Following a 20 minute kinase reaction, 50 µl of the luminescent buffer reagent was added to each well and allowed to incubate for 10 minutes prior to reading luminescence.

Figure 7:
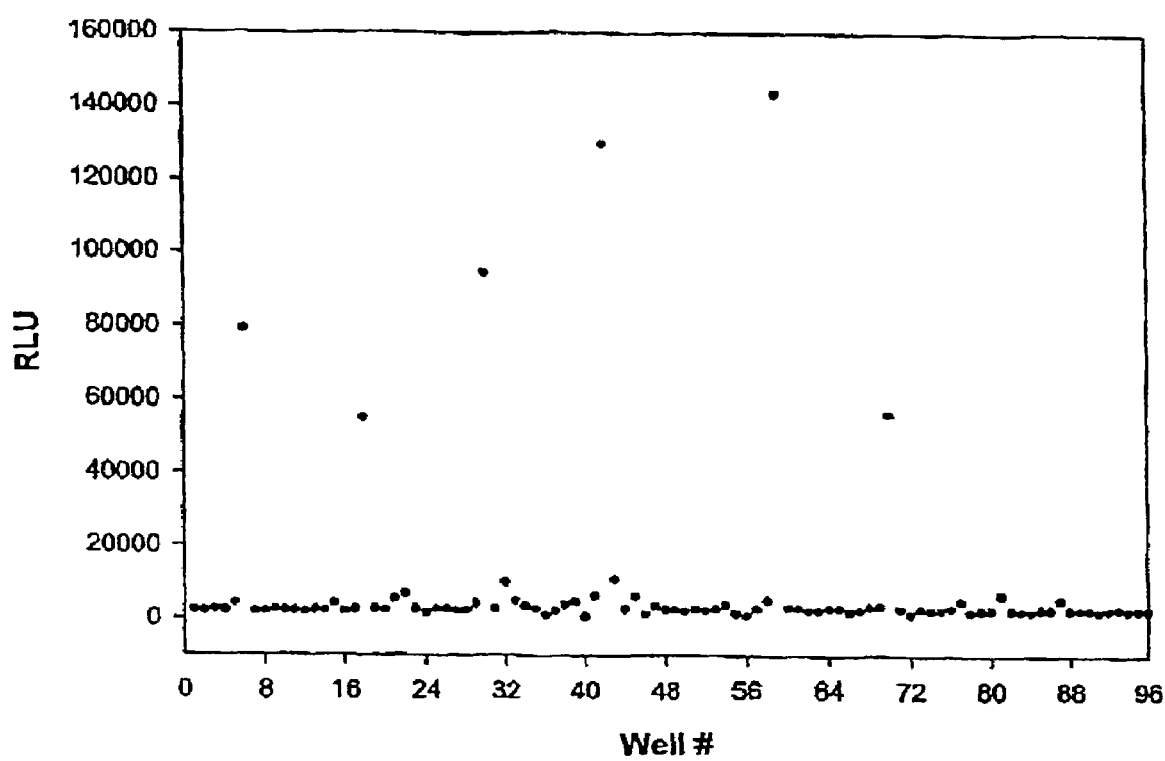
FIG. 7 illustrates the results of a Protein Kinase Inhibition Screening Study according to the present invention with known inhibitors of PKA.

Six "hits" or positives were identified (RLU>40,000). From left to right, on FIG. 7, the positive compounds are HA-1004 hydrochloride, H-7 dihydrochloride, H-8 dihydrochloride, and H-9 dihydrochloride, U-73122, and GW5074. The first 4 compounds are well known inhibitors of PKA. Accordingly, it is clear from the results shown in FIG. 7, that inhibitors of kinases can be easily and quickly identified using the method of the present invention. With respect to the additional positive compounds, U-73122 is a known inhibitor of Phospholipase C, A2 and GW5074 is a known inhibitor of cRafl kinase. To confirm whether these two additional compounds are also inhibitors of PKA, each of these compounds could be titrated with PKA to determine their $IC_{50}$ values.

Example 8

Determining Stability of Kinase Signal

Figure 8:
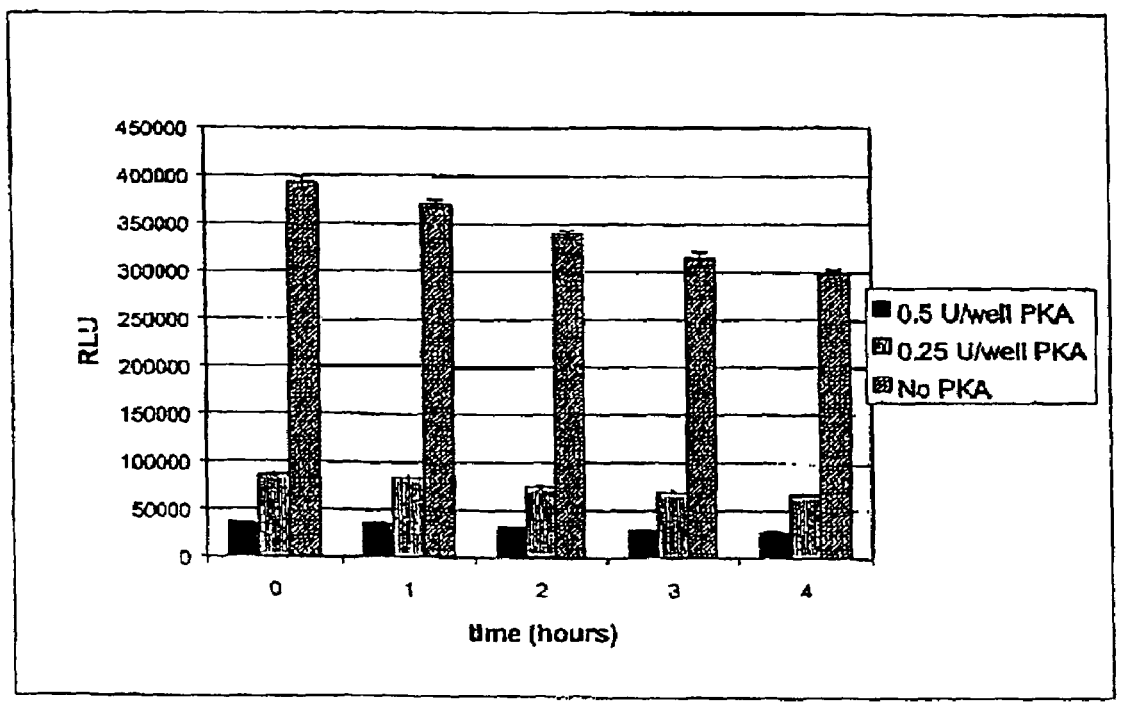
FIG. 8 illustrates the results of the signal stability of a PKA assay according to the present invention as measured over time.

As discussed above, the present invention provides the user with stable luminescent readout over long periods of time, making it possible to stack well-plates. In this example, commercially available PKA was assessed in a 96 well plate (n=32). Kinase reactions were performed in 40 mM Tris-HCl (pH 7.5), 20 mM $MgCl_2$, 0.1 mg/ml BSA, 5 µM kemptide (LRRASLG), and 1 µM ATP with either no PKA, 0.25 U/well PKA, or 0.5 U/well PKA. The final kinase reaction volume was 50 µl. Following a 20 minute kinase reaction, 50 µl of the luminescent buffer reagent of Example 1 was added to each well and allowed to incubate for 10 minutes prior to reading luminescence at the indicated times. Signal loss at 4 hours was <25%. FIG. 8 shows that the luminescent signal is quite stable over time, making the method of the invention very useful in automated procedures.

REFERENCES

Aiginger, P., R. Kuzmits, H. Lang, and M. M. Muller. 1980. Changes in the ATP content of leukaemic cells induced by cytotoxic substances. *J. Clin. Chem. Clin. Biocehm.* 1:216.

Andreotti, P. E., I. A. Cree, C. M. Kurbacher, D. M. Hartmann, D. Linder, G. Harel, I. Gleiberman, P. A. Caruso, S. H. Ricks, M. Untch, and et al. 1995. Chemosensitivity testing of human tumors using a microplate adenosine triphosphate luminescence assay: clinical correlation for cisplatin resistance of ovarian carcinoma. *Cancer Res.* 55:5276-82.

Ausubel, F. M., R. Brent, R. E. Kingston, D. D. Moore, J. G. Seidman, J. A. Smith, and K. Struhl. 1987. Current protocols in molecular biology. John Wiley & Sons, New York.

Baldwin, T. O., and V. A. Green. 2000. Purification of firefly luciferase from recombinant sources. *Methods Enzymol.* 305:180-8.

Beny, M., and M. Dolivo. 1976. Separation of firefly luciferase using an anion exchanger. *FEBS Lett.* 70:167-70.

Bostick, W. D., M. S. Denton, and S. R. Dinsmore. 1982. Liquid-chromatographic separation and bioluminescent detection of creatine kinase isoenzymes. In Bioluminescence and Chemiluminescence: Instruments and Applications. Vol. II. K. Van Dyke, editor. CRC Press, Boca Raton, Fla. 227-246.

Bowie, L. J., V. Horak, and M. De Luca. 1973. Synthesis of a new substrate analog of firefly luciferin. An active-site probe. *Biochemistry.* 12:1845-52.

Bradbury, D. A., T. D. Simmons, K. J. Slater, and S. P. Crouch. 2000. Measurement of the ADP:ATP ratio in human leukaemic cell lines can be used as an indicator of cell viability, necrosis and apoptosis. *J Immunol Methods.* 240:79-92.

Branchini, B. R. 2000. Chemical synthesis of firefly luciferin analogs and inhibitors. *Methods Enzymol.* 305:188-95.

Branchini, B. R., M. M. Hayward, S. Bamford, P. M. Brennan, and E. J. Lajiness. 1989. Naphthyl- and quinolylluciferin: green and red light emitting firefly luciferin analogues. *Photochem Photobiol.* 49:689-95.

Branchini, B. R., T. M. Marschner, and A. M. Montemurro. 1980. A convenient affinity chromatography-based purification of firefly luciferase. *Anal Biochem.* 104:386-96.

Carter, P. 1986. Site-directed mutagenesis. *Biochem J.* 237:1-7.

Craig, F. F., A. C. Simmonds, D. Watmore, F. McCapra, and M. R. White. 1991. Membrane-permeable luciferin esters for assay of firefly luciferase in live intact cells. *Biochem J.* 276:637-41.

Cree, I. A. 1998. Luminescence-based cell viability testing. *Methods Mol Biol.* 102:169-77.

Cree, I. A., and P. E. Andreotti. 1997. Measurement of Cytotoxicity by ATP-based Luminescence Assay in Primary Cell Cultures and Cell Lines. *Toxicology in Vitro.* 11:553-556.

Crouch, S. P., R. Kozlowski, K. J. Slater, and J. Fletcher. 1993. The use of ATP bioluminescence as a measure of cell proliferation and cytotoxicity. *J Immunol Methods.* 160:81-8.

Demerec, M., E. A. Adelberg, A. J. Clark, and P. E. Hartman. 1966. A proposal for a uniform nomenclature in bacterial genetics. *Genetics.* 54:61-76.

Ebadi, M. S. 1972. Firefly luminescence in the assay of cyclic AMP. *Adv Cyclic Nucleotide Res.* 2:89-109.

Filippova, N. Y., A. F. Dukhovich, and N. N. Ugarova. 1989. New approaches to the preparation and application of firefly luciferase. *J Biolumin Chemilumin.* 4:419-22.

Hastings, J. W. 1996. Chemistries and colors of bioluminescent reactions: a review. *Gene.* 173:5-11.

Hastings, J. W., and T. Wilson. 1976. Bioluminescence and chemiluminescence. *Photochem Photobiol.* 23:461-73.

Jassim, S. A., A. Ellison, S. P. Denyer, and G. S. Stewart. 1990. In vivo bioluminescence: a cellular reporter for research and industry. *J Biolumin Chemilumin.* 5:115-22.

Jones, K., F. Hibbert, and M. Keenan. 1999. Glowing jellyfish, luminescence and a molecule called coelenterazine. *Trends Biotechnol.* 17:477-81.

Kajiyama, N., and E. Nakano. 1993. Thermostabilization of firefly luciferase by a single amino acid substitution at position 217. *Biochemistry.* 32:13795-9.

Kajiyama, N., and E. Nakano. 1994. Enhancement of thermostability of firefly luciferase from Luciola lateralis by a single amino acid substitution. *Biosci Biotechnol Biochem.* 58:1170-1.

Kangas, L., M. Gronroos, and A. L. Nieminen. 1984. Bioluminescence of cellular ATP: a new method for evaluating cytotoxic agents in vitro. *Med Biol.* 62:338-43.

Kiechle, F. L., L. Jarett, D. A. Popp, and N. Kotagal. 1980. Isolation from rat adipocytes of a chemical mediator for insulin activation of pyruvate dehydrogenase. *Diabetes.* 29:852-5.

Kricka, L. J., and M. De Luca. 1982. Effect of solvents on the catalytic activity of firefly luciferase. Arch Biochem Biophys. 217:674-81.

Lundin, A., J. Anson, and P. Kau. 1994. ATP extractants neutralised by cyclodextrins. In Bioluminescence and Chemiluminescence: Fundamental and Applied Aspects. A. K. Campbell, L. J. Kricka, and P. E. Stanley, editors. John Wily & Sons, New York. 399-402.

McElroy, W. D., H. H. Seliger, and E. H. White. 1969. Mechanism of bioluminescence, chemiluminescence and enzyme function in the oxidation of firefly luciferin. *Photochem Photobiol.* 10:153-70.

Miska, W., and R. Geiger. 1987. Synthesis and characterization of luciferin derivatives for use in bioluminescence enhanced enzyme immunoassays. New ultrasensitive detection systems for enzyme immunoassays, I. *J Clin Chem Clin Biochem.* 25:23-30.

Missiaen, L., F. Wuytack, H. De Smedt, M. Vrolix, and R. Casteels. 1988. AlF4-reversibly inhibits 'P'-type cation-transport transferases, possibly by interacting with the phosphate-binding site of the transferase. *Biochem J.* 253: 827-33.

Morii, M., and N. Takeguchi. 1993. Different biochemical modes of action of two irreversible H+,K(+)-transferase quenching agents, omeprazole and E3810. *J Biol Chem.* 268:21553-9.

Moyer, J. D., and J. F. Henderson. 1983. Nucleoside triphosphate specificity of firefly luciferase. *Anal Biochem.* 131: 187-9.

Nguyen, V. T., M. Morange, and O. Bensaude. 1988. Firefly luciferase luminescence assays using scintillation counters for quantitation in transfected mammalian cells. *Anal Biochem.* 171:404-8.

Petty, R. D., L. A. Sutherland, E. M. Hunter, and I. A. Cree. 1995. Comparison of MTT and ATP-based assays for the measurement of viable cell number. *J Biolumin Chemilumin.* 10:29-34.

Picciolo, G. L., E. W. Chappelle, R. R. Thomas, and M. A. McGarry. 1977. Performance characteristics of a new photometer with a moving filter tape for luminescence assay. *Appl Environ Microbiol.* 34:720-4.

Ronner, P., E. Friel, K. Czerniawski, and S. Frankle. 1999. Luminometric assays of ATP, phosphocreatine, and creatine for estimation of free ADP and free AMP. *Anal Biochem.* 275:208-16.

Sambrook, J. 1989. Molecular cloning: a laboratory manual. Cold Spring Harbor Laboratory, Cold Spring Harbor.

U.S. Pat. No. 5,618,682. 1997. BIOLUMINESCENCE MEASUREMENT SYSTEM. US.

U.S. Pat. No. 5,866,348. 1999. BIOLUMINESCENCE MEASUREMENT SYSTEM. US.

Simpson, W. J., and J. R. Hammond. 1991. The effect of detergents on firefly luciferase reactions [published erratum appears in J Biolumin Chemilumin July-September 1991; 6(3): 146]. *J Biolumin Chemilumin.* 6:97-106.

Stanley, P. E. 1989. A review of bioluminescent ATP techniques in rapid microbiology. *J Biolumin Chemilumin.* 4:375-80.

Tamaoki, T. 1991. Use and specificity of staurosporine, UCN-01, and calphostin C as protein kinase inhibitors. *Methods in Enzymology* 201, 304-16.

Thomson, C. M., P. J. Herring, and A. K. Campbell. 1997. The widespread occurrence and tissue distribution of the imidazolopyrazine luciferins. *J Biolumin Chemilumin.* 12:87-91.

WO 00/18953. 2000. Method for detecting ATP. PCT.

Vaskinn, S., E. Sundkvist, R. Jaeger, and G. Sager. 1999. The effect of Mg2+, nucleotides and transferase quenching agents on the uptake of [3H]-cGMP to inside-out vesicles from human erythrocytes. *Mol Membr Biol.* 16:181-8.

Wells, J. A., M. Vasser, and D. B. Powers. 1985. Cassette mutagenesis: an efficient method for generation of multiple mutations at defined sites. *Gene.* 34:315-23.

White, E. H., E. Rapaport, T. A. Hopkins, and H. H. Seliger. 1969. Chemi- and bioluminescence of firefly luciferin. *J Am Chem Soc.* 91:2178-80.

White, H. E., J. D. Miano, and M. Umbreit. 1975. Letter: on the mechanism of firefly luciferin luminescence. *J Am Chem Soc.* 97:198-200.

White, P. J., D. J. Squirrell, P. Arnaud, C. R. Lowe, and J. A. Murray. 1996. Improved thermostability of the North American firefly luciferase: saturation mutagenesis at position 354. *Biochem J.* 319:343-50.

Wilson, T., and J. W. Hastings. 1998. Bioluminescence. *Annu Rev Cell Dev Biol.* 14:197-230.

U.S. Pat. No. 5,283,179. 1994. LUCIFERASE ASSAY METHOD. US.

U.S. Pat. No. 5,650,289. 1997. LUCIFERASE ASSAY COMPOSITIONS. US.

WO 9914336. 1999. Thermostable luciferases and methods of production. PCT.

Wood, K. V., Y. A. Lam, and W. D. McElroy. 1989. Introduction to beetle luciferases and their applications. *J Biolumin Chemilumin.* 4:289-301.

Yang, J., and D. B. Thomason. 1993. An easily synthesized, photolyzable luciferase substrate for in vivo luciferase activity measurement. *Biotechniques.* 15:848-50.

Ye, L., L. M. Buck, H. J. Schaeffer, and F. R. Leach. 1997. Cloning and sequencing of a cDNA for firefly luciferase from Photuris pennsylvanica. *Biochim Biophys Acta.* 1339:39-52.

Zoller, M. J., and M. Smith. 1987. Oligonucleotide-directed mutagenesis: a simple method using two oligonucleotide primers and a single-stranded DNA template. *Methods Enzymol.* 154:329-50.

What is claimed is:

1. A method for measuring ATP-dependent transferase enzymatic activity comprising:
(a) providing a reagent composition comprising a detergent, a luminogenic molecule and a chemostable luciferase, wherein the detergent selectively stops ATP-dependent transferase activity without substantially affecting chemostable luciferase activity;
(b) incubating a first reaction mixture comprising an ATP-dependent transferase, ATP, and a transferase substrate for a first predetermined time period under conditions effective to allow for a transferase reaction to occur;
(c) contacting the first reaction mixture with the reagent composition to form a second reaction mixture and incubating the second reaction mixture for a second predetermined time period under conditions effective to simultaneously stop ATP-dependent transferase enzymatic activity and allow for a bioluminescent reaction to occur; and (d) determining transferase activity by measuring luminescence of the second reaction mixture.

2. A method for screening a compound for its effect on ATP-dependent transferase enzymatic activity comprising:
(a) providing a compound for screening;
(b) providing a reagent composition comprising a detergent, a luminogenic molecule and a chemostable luciferase, wherein the detergent selectively stops ATP-dependent transferase activity without substantially affecting chemostable luciferase activity;
(c) incubating a first reaction mixture comprising an ATP-dependent transferase, ATP, a transferase substrate, and the compound for a first predetermined time period under conditions effective to allow for an ATP-dependent transferase reaction to occur;
(d) contacting the first reaction mixture with the reagent composition to form a second reaction mixture and incubating the second reaction mixture for a second predetermined time period under conditions effective to simultaneously stop ATP-dependent transferase enzymatic activity and allow for a bioluminescent reaction to occur; and
(e) determining the effect of the compound on ATP-dependent transferase activity by measuring and comparing luminescence of the second reaction mixture relative to a control mixture having no compound.

3. A high throughput method for rapidly screening a plurality of compounds to determine their effect on ATP-dependent transferase enzymatic activity comprising:
(a) providing a plurality of compounds for screening;
(b) providing a reagent composition comprising a detergent, a luminogenic molecule and a chemostable luciferase, wherein the detergent selectively stops ATP-dependent transferase activity without substantially affecting chemostable luciferase activity;
(c) incubating a plurality of first reaction mixtures, each first reaction mixture comprising an ATP-dependent transferase, ATP, transferase substrate, and at least one compound, for a first predetermined time period under conditions effective to allow for ATP-dependent transferase enzymatic reactions to occur;
(d) contacting for a second predetermined time period the first reaction mixtures with the reagent composition to form a plurality of second reaction mixtures under conditions effective to simultaneously stop ATP-dependent transferase enzymatic activity and allow for bioluminescent reactions to occur; and
(e) determining the effect of the compounds on ATP-dependent transferase activity by measuring and comparing luminescence of the second reaction mixtures relative to at least one control mixture having no compound.

4. The method of any one of claims 1, 2, or 3 wherein the transferase enzymatic activity comprises kinase activity or ion channel/pump activity.

5. The method of claim 4 wherein the transferase enzymatic activity comprises protein kinase activity, lipid kinase activity, polynucleotide kinase activity, or sugar kinase activity.

6. The method of claim 5 wherein the protein kinase comprises a Ser/Thr protein kinase, a protein tyrosine kinase, or a protein lipid-dependent kinase.

7. The method of claim 6 wherein the Ser/Thr protein kinase comprises cAMP-dependent protein kinase (PKA), calcium and phosphlipids dependent protein kinase (PKC), cGMP-dependent protein kinase (PKG), calcium and calmodulin dependent protein kinase (CaM KII) or a dual specificity protein kinase.

8. The method of claim 7 wherein the dual specificity protein kinase comprises mitogen activated protein kinase (MAPK) or mitogen activated protein kinase kinase(MEK).

9. The method of claim 6 wherein the tyrosine kinase comprises Rous sarcoma related protein kinases(Src), or Src family protein tyrosine kinases.

10. The method of claim 9 wherein the Src family protein tyrosine kinases comprise Src, Lck, Fyn, or Lyn.

11. The method of claim 6 wherein the tyrosine kinase comprises epidermal growth factor receptor(EGFR), platelet derived growth factor receptor(PDGFR) or steel growth factor receptor(c-KIT).

12. The method of claim 1 wherein the detergent comprises a cationic detergent, anionic detergent, or zwitterionic detergent.

13. The method of claim 12 wherein the cationic detergent comprises dodecyltrimethylammonium bromide, cetyltrimethylammonium bromide or benzyldimethyldodecylammonium bromide.

14. The method of claim 13 wherein the cationic detergent is dodecyltrimethylammonium bromide.

15. The method of claim 12 wherein the anionic detergent comprises SDS or deoxycholate.

16. The method of claim 12 wherein the zwitterionic detergent comprises sulfobetaine 3-10.

17. The method of any one of claims 1, 2, or 3 wherein the luminogenic molecule comprises D-luciferin or a luciferin derivative.

18. The method of any one of claims 1, 2, or 3 wherein the transferase itself is being phosphorylated or the transferase substrate is being phosphorylated.

19. The method of any one of claims 2 or 3 wherein the compound enhances transferase enzymatic activity.

20. The method of any one of claims 2 or 3 wherein the compound inhibits transferase enzymatic activity.

* * * * *